US011202885B2

(12) United States Patent
Oliverius et al.

(10) Patent No.: US 11,202,885 B2
(45) Date of Patent: Dec. 21, 2021

(54) TENSION ADJUSTMENT FOR STEERING ACTUATOR FOR DEFLECTABLE CATHETER

(71) Applicant: St. Jude Medical, Cardiology Division, Inc., St. Paul, MN (US)

(72) Inventors: Andrew R. Oliverius, Eagan, MN (US); Russell D. Terwey, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 358 days.

(21) Appl. No.: 16/160,794

(22) Filed: Oct. 15, 2018

(65) Prior Publication Data

US 2019/0111236 A1  Apr. 18, 2019

Related U.S. Application Data

(60) Provisional application No. 62/572,868, filed on Oct. 16, 2017.

(51) Int. Cl.
*A61M 25/01* (2006.01)
*A61B 18/14* (2006.01)
*A61B 34/00* (2016.01)

(52) U.S. Cl.
CPC .... *A61M 25/0113* (2013.01); *A61M 25/0136* (2013.01); *A61M 25/0147* (2013.01); *A61B 18/1492* (2013.01); *A61B 2034/715* (2016.02)

(58) Field of Classification Search
CPC .......... A61B 2034/715; A61B 17/8869; A61B 17/8897; A61B 18/1492; A61M 25/0113; A61M 25/0136; A61M 25/0147
See application file for complete search history.

(56) References Cited

U.S. PATENT DOCUMENTS

| 9,308,031 B2* | 4/2016 | Elghazaly .......... A61B 17/7241 |
| 10,122,096 B2* | 11/2018 | Ruland .................... H01R 4/36 |
| 2005/0004515 A1 | 1/2005 | Hart et al. |

(Continued)

FOREIGN PATENT DOCUMENTS

| CN | 105188827 A | 12/2015 |
| CN | 107206597 A | 9/2017 |

(Continued)

*Primary Examiner* — Nathan R Price
*Assistant Examiner* — Melissa A Snyder
(74) *Attorney, Agent, or Firm* — Dykema Gossett PLLC

(57) ABSTRACT

A tuning pin for a steering actuator comprising a head portion proximate a proximal end of the tuning pin, the head portion comprising an anti-rotation element, a body portion distal the head portion, the body portion comprising a through hole, and a tip portion distal the body portion and proximate a distal end of the tuning pin, the tuning pin configured to couple with a pin block in the steering actuator. A system comprising a catheter, and a steering actuator comprising a tuning pin, the tuning pin comprising a head portion proximate a proximal end of the tuning pin, the head portion comprises an anti-rotation element, a body portion distal the head portion, where the body portion comprises a through hole, and a tip portion distal the body portion and proximate a distal end of the tuning pin, wherein the tuning pin is configured to couple with a pin block.

10 Claims, 20 Drawing Sheets

(56) References Cited

U.S. PATENT DOCUMENTS

| | | | |
|---|---|---|---|
| 2007/0197896 A1* | 8/2007 | Moll | A61B 1/00039 |
| | | | 600/407 |
| 2007/0277921 A1 | 12/2007 | Hart et al. | |
| 2007/0299427 A1 | 12/2007 | Yeung et al. | |
| 2010/0069834 A1* | 3/2010 | Schultz | A61M 25/0147 |
| | | | 604/95.04 |
| 2012/0197255 A1 | 8/2012 | Elghazaly | |
| 2014/0336573 A1 | 11/2014 | Yu et al. | |
| 2017/0113017 A1 | 7/2017 | Zhang et al. | |

FOREIGN PATENT DOCUMENTS

| | | |
|---|---|---|
| EP | 3 263 296 A1 | 1/2019 |
| JP | S60-100701 U | 7/1985 |
| WO | 2004/096015 A2 | 11/2004 |
| WO | 2016136430 A1 | 9/2016 |

* cited by examiner

TENSION ADJUSTMENT FOR STEERING ACTUATOR FOR DEFLECTABLE CATHETER

CROSS-REFERENCE TO RELATED APPLICATIONS

This application claims the benefit of U.S. provisional application No. 62/572,868, filed 16 Oct. 2017, which is hereby incorporated by reference as though fully set forth herein.

BACKGROUND a. Field

This disclosure relates to apparatuses and systems for deflectable catheters. In particular, the instant disclosure relates to steering actuators for deflectable catheters.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. These lesions disrupt undesirable cardiac activation pathways and thereby limit, corral, or prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal edge tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal edge tip can be deflected by a pull wire attached at the distal end of the catheter and extending proximally to an actuator in a control handle that controls the application of tension on the pull wire.

The foregoing discussion is intended only to illustrate the present field and should not be taken as a disavowal of claim scope.

BRIEF SUMMARY

The instant disclosure, in at least one embodiment, a tuning pin for a steering actuator comprises a head portion proximate a proximal end of the tuning pin, where the head portion comprises an anti-rotation element, a body portion distal of the head portion, where the body portion comprises a through hole, and a tip portion distal of the body portion and proximate a distal end of the tuning pin, wherein the tuning pin is configured to couple with a pin block in the steering actuator.

In another embodiment, a system comprises a catheter, and a steering actuator comprising a tuning pin, where the tuning pin comprises a head portion proximate a proximal end of the tuning pin, where the head portion comprises an anti-rotation element, a body portion distal of the head portion, where the body portion comprises a through hole, and a tip portion distal of the body portion and proximate a distal end of the tuning pin, wherein the tuning pin is configured to couple with a pin block in the steering actuator.

DETAILED DESCRIPTION OF EMBODIMENTS

Figure 1:
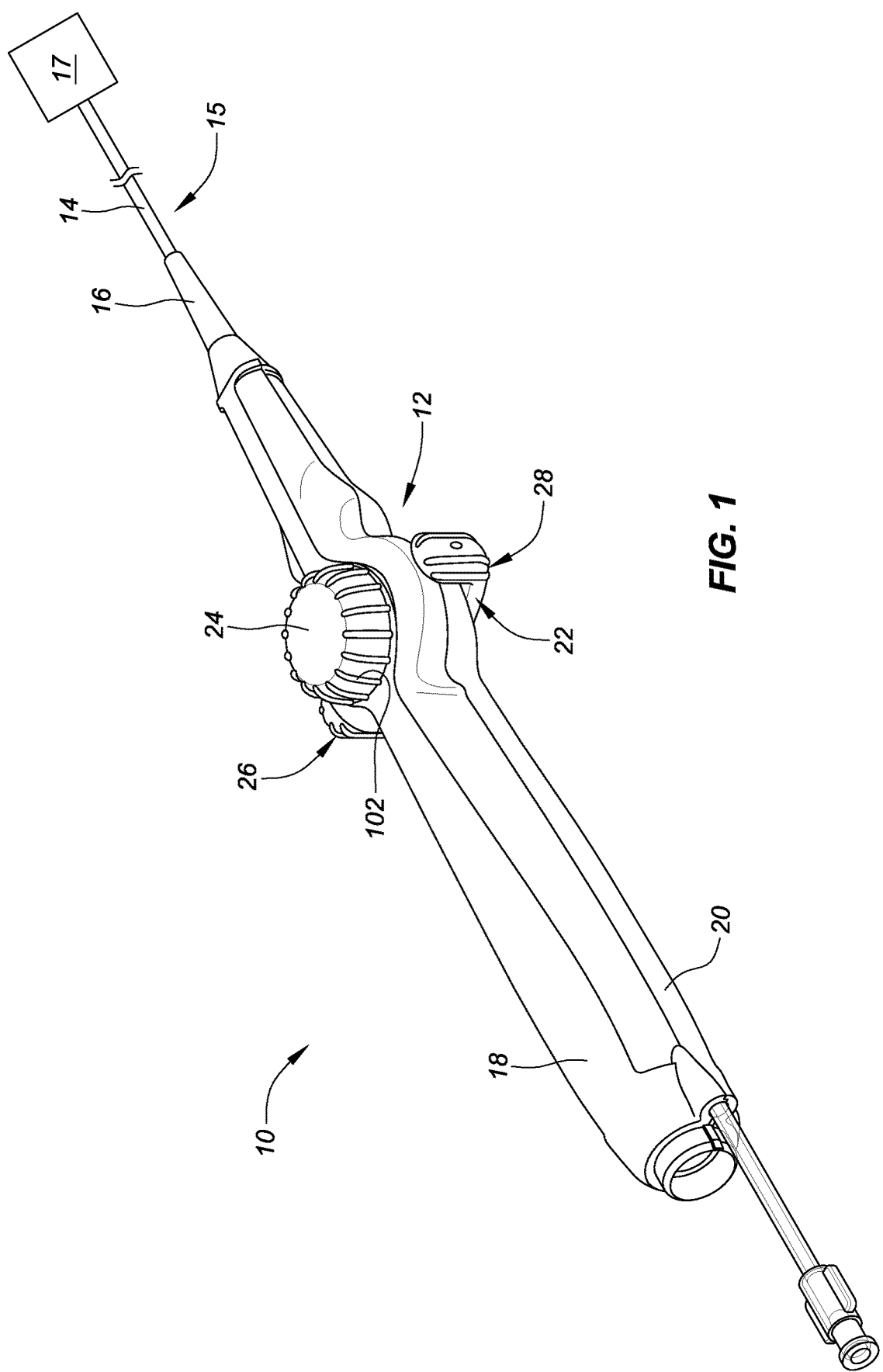
FIG. 1 is an isometric view of a catheter handle having a steering actuator for deflecting a catheter shaft.

Referring now to the figures, in which like reference numbers refer to the same or similar features in the various views, FIG. 1 is an isometric view of a catheter handle 10 comprising a steering actuator 12 for deflecting a catheter shaft 14. In FIG. 1, only a short section of a proximal end portion 15 of the catheter shaft 14 is actually depicted distal of a strain relief 16, and the deflectable section or tip of the catheter shaft is shown schematically by box 17. As shown in this figure, the handle comprises an upper handle housing 18 and a lower handle housing 20. A steering actuator 12 is pivotally sandwiched between the upper and lower handle housings, and includes an outer actuator 22 and an outer knob 24. The outer actuator 22 defines a first boss 26 and a second boss 28 that a user (e.g., an electrophysiologist or other clinician) uses to effect deflection of the catheter shaft. One such steering actuator may be seen by reference to U.S. patent application Ser. No. 14/272,412, filed 7 May 2014, entitled "Steering Actuator for Deflectable Catheter," which is hereby incorporated by reference in its entirety as though fully set forth herein.

Figure 2:
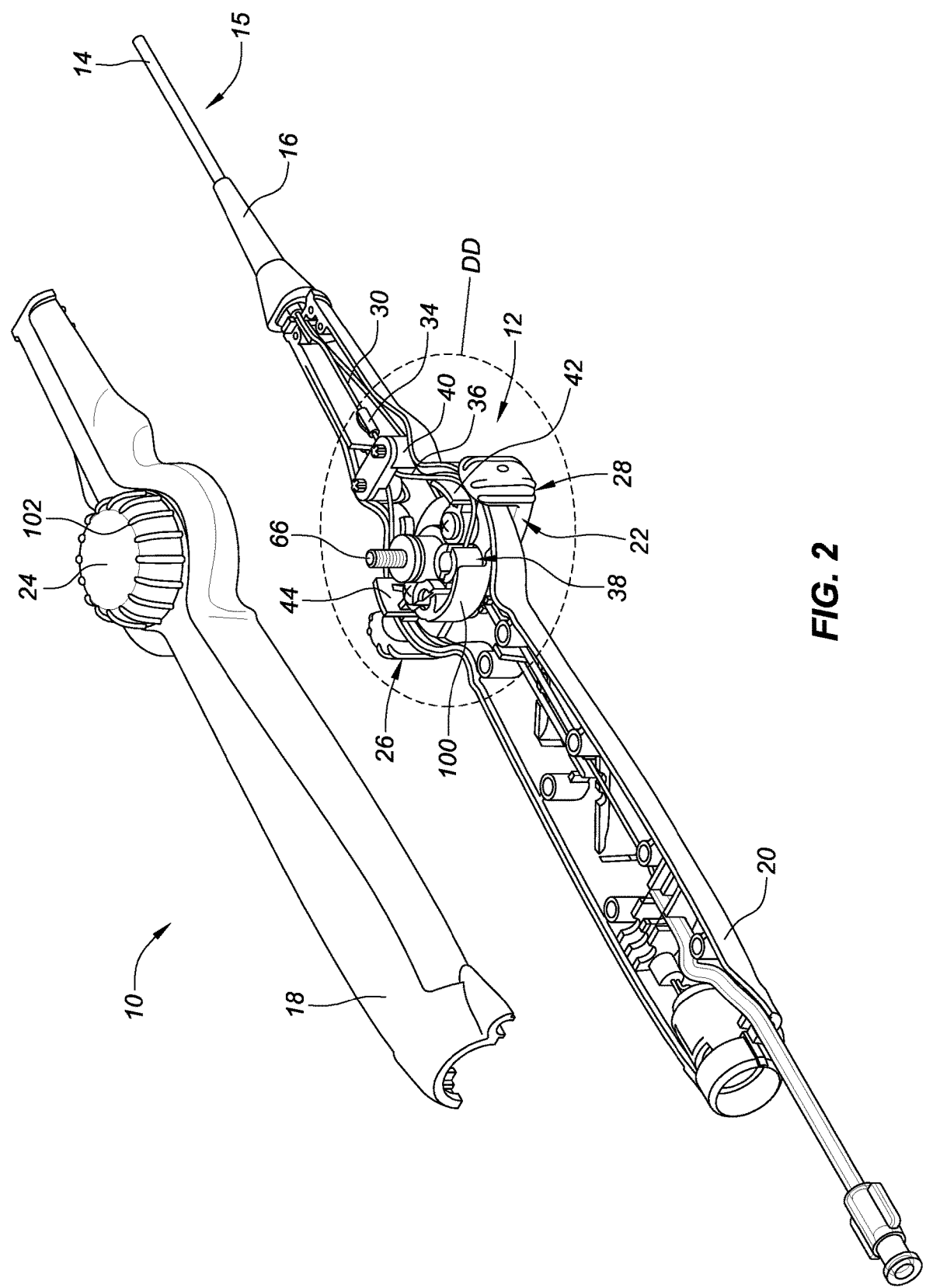
FIG. 2 is an isometric view of the catheter handle and actuator depicted in FIG. 1, but with the upper handle housing exploded away from the handle to reveal internal components of the steering actuator.

FIG. 2 also depicts the representative catheter handle 10 and steering actuator 12 shown in FIG. 1, but with the upper handle housing exploded away from the rest of the handle, revealing several components of the actuator. As shown in this figure, the proximal end portion 15 of the catheter shaft 14 is supported by a strain relief 16. Pull wires 30, 32 (both more clearly visible in FIG. 4), which extend from the handle down the catheter shaft to an anchor point (not shown) in a deflectable section (see 17 in FIG. 1) of the catheter, enter the handle from its distal end. In this embodiment, each pull wire is then attached by a connecting member, such as a crimp 34, to a fiber 36 that extends from the crimp to an anchor point 38 (e.g., a tensioning mechanism, embodiments of which are described more fully below). The fiber comprises a durable material that is selected to handle the circuitous path (and concomitant stresses) that the fiber follows from the crimp 34 to the anchor point 38. As will be discussed further below, each fiber passes over a roller 40 (or pull-wire-deflection surface), then passes around a wall section (or guide wall or pull wire guide wall) 42 before reaching one of the anchor points 38. In the embodiment shown in FIG. 2, the first and second wall sections (or guide walls) 42, 44 comprise arc wall sections or "wing wall" sections. These wall sections increase the length of the path traversed by the fiber (or a pull wire) after passing the roller on its way to the mounting point of the proximal portion of the fiber.

Figure 3:
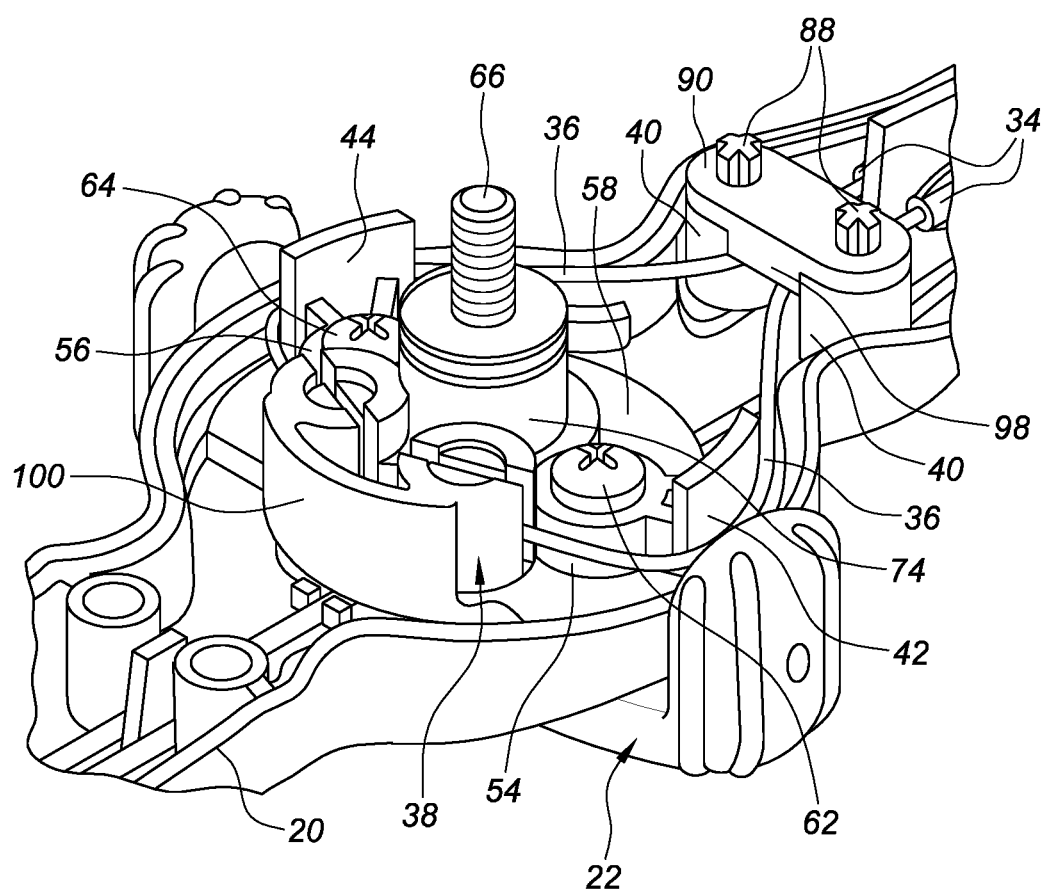
FIG. 3 is a fragmentary, isometric view of the steering actuator, consistent with embodiments of the present disclosure.
Figure 4:
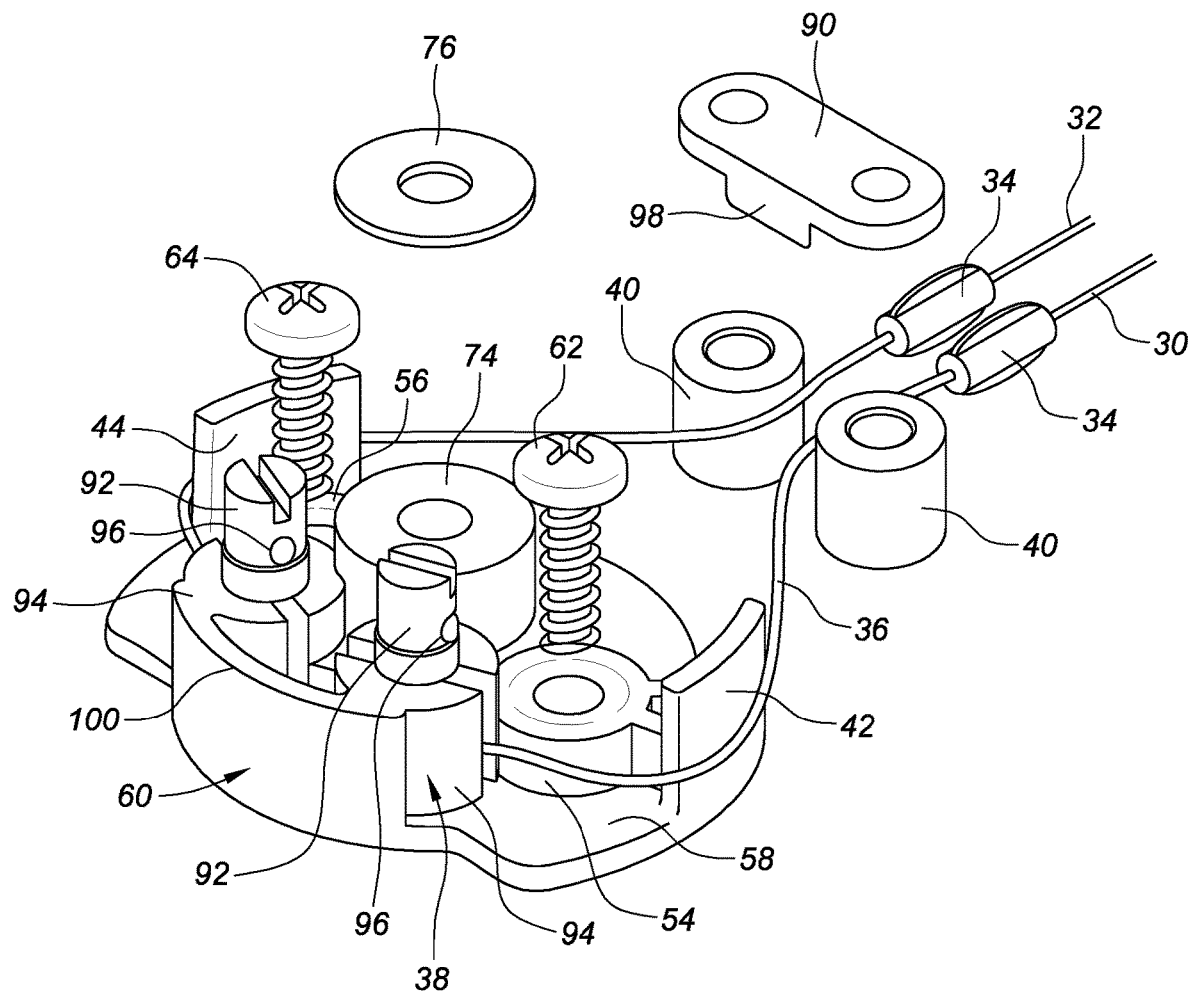
FIG. 4 is a fragmentary, isometric view of the portion of the catheter handle and steering actuator in dashed circle AA in FIG. 2 including an inner actuator, consistent with embodiments of the present disclosure.

FIG. 3 is a fragmentary, isometric view of a steering actuator, consistent with embodiments of the present disclosure. Referring next to FIGS. 3 and 4, further details of a representative inner actuator and the various components that it supports will be described. FIG. 4 is a fragmentary, isometric view of the portion of the catheter handle and steering actuator in dashed circle DD in FIG. 2 including an inner actuator, consistent with embodiments of the present disclosure. Starting at the upper right portion of FIG. 4, it is possible to see two crimps (each labeled 34) that connect the first and second pull wires 30, 32 to the fibers (each labeled 36), respectively. Each fiber then extends around a respective roller 40 before passing around a wall section 42, 44 and then to an anchor point 38 that is part of an inner actuator 60.

In this embodiment, each anchor point comprises a pull wire tensioning or tension mechanism (e.g., a pull wire "tuner mechanism" or a pull wire termination) that, in one embodiment, includes a tension adjustment pin 92 (e.g., a "tuning pin" or a "tuner pin") and a pin block 94 (also part of the inner actuator 60). As shown in FIGS. 3 and 4, each tension adjustment pin may be rotated into its respective pin block. The tension adjustment pins and pin blocks may include screw threads. That is, both the tension adjustment pin and the pin block comprising a tensioning mechanism may be threaded, or either the tension adjustment pin or the pin block comprising a tensioning mechanism may be threaded, or neither the tension adjustment pin nor the pin block comprising a tensioning mechanism may be threaded.

In the embodiment depicted in FIGS. 3 and 4, the pin blocks each comprise a slotted pillar. In particular, each pin block comprises a hollow cylinder with a slot or cut through opposing locations of the cylinder wall, the cut also passing through the center of the pillar. As may be seen to good advantage in FIG. 4, each tension adjustment pin comprises a fiber channel or hole 96. Each fiber is connected to the tensioning mechanism by inserting a proximal portion of the fiber into the corresponding hole or channel in the tuner pin, and then rotating the tuner pin in the pin block, which traps the fiber between the outer surface of the tuner pin and the inner surface of the pin block. The slots in the cylindrical walls of the pin blocks allow the walls to flex slightly as the fiber is wound onto a respective tuner pin. This allows the fibers, and thus the pull wires, to be preloaded with a desired tension. This system simplifies manufacturing by allowing for less precise initial trimming of the fibers (or pull wires) since adjustments can be made via the tensioning mechanisms. The tensioning mechanisms allow for easy termination of the fiber ends and permit precise preloading of desired tension on the pull wires.

As also may be seen to good advantage in FIG. 3, the roller retention cap 90 includes a guide wall 98 that extends downwardly (as depicted in FIG. 3) to keep the fibers at a desired trajectory toward the first and second guide wall sections. As may also be seen to good advantage in FIG. 3, each roller pin 88 has a cross-sectional area in the shape of a cross, for example, rather than a circle. This cross-sectional shape for the roller pins helps reduce friction between the outer surface of the roller pins and the inner surface of the rollers. It should be noted that each roller may be replaced with a fixed cylinder that does not rotate on a roller pin, or by an arcuate guiding surface configured to guide one of the fibers on the desired trajectory toward its respective wall sections. It should also be kept in mind that each of the pull wires could traverse the entire course from its anchor point at the distal end of the catheter to its anchor point in the handle (e.g., at one of the tensioning mechanisms shown to best advantage in FIGS. 4 and 5).

Figure 5:
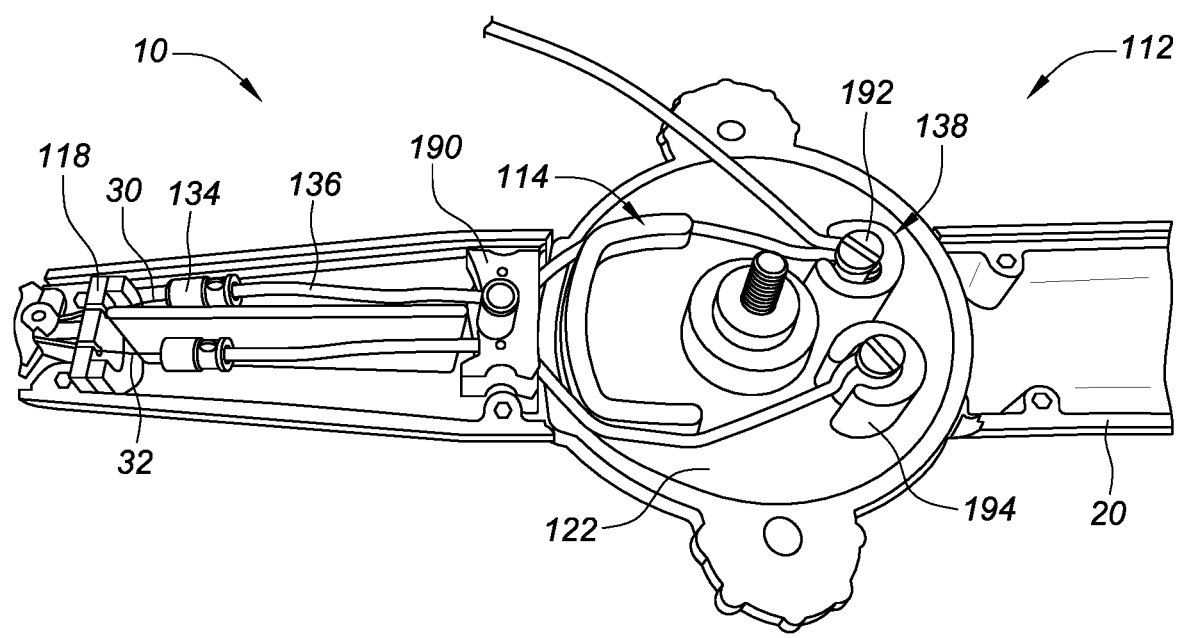
FIG. 5 is a fragmentary, isometric view of the catheter handle and steering actuator depicted in FIG. 1, with the upper handle housing removed and with an upper actuator removed to reveal details about the steering actuator, consistent with embodiments of the present disclosure.

FIG. 5 is a fragmentary, isometric view of the catheter handle and steering actuator depicted in FIG. 1, with the upper handle housing removed and with an upper actuator removed to reveal details about the steering actuator, consistent with embodiments of the present disclosure. As oriented in FIG. 5, the steering wires enter the handle from the left side of the figure. The distal ends (not shown) of the pull wires would be anchored to a deflectable catheter shaft section at or near a distal end of the catheter. The proximal end of each pull wire, as depicted in FIG. 5, is attached to a corresponding fiber 136 via a crimp 134. In all of the disclosed embodiments, alternative techniques could be used to attach each pull wire to its respective fiber, or each pull wire could extend the entire length from its distal anchor point (not shown) to its proximal anchor point.

The steering actuator 112 depicted in FIG. 5 is similar to the actuator described above. However, in this embodiment, a single, C-shaped or U-shaped (or flattened-semicircular-shaped or horseshoe-shaped) guide wall 114 is present. The shape of the guide wall 114 may be any shape that enables the fiber/pull wire to be taken up or let out upon manipulation of the actuator (e.g., rotation of the inner actuator in this embodiment). For example, the front wall of the illustrated U-shaped guide wall 114 could be removed in whole or in part, while the side portions of the guide wall 114 are used to further tension or relax their respective pull wires when the actuator is rotated one way or the other. The shape of the guide wall 114 allows the fiber (or pull wire if no fiber is used) to follow a fairly straight path. This helps reduce bending of the fiber (or pull wire). When the actuator is rotated in the handle housing during use of the catheter, the fiber starts wrapping at the outer radius, and not at the flattened sides. Thus, the travel gain is on the outside radius of the guide wall. The outer radius of the guide wall is at the same radial distance as if the guide wall were semicircular.

In the steering actuator depicted in FIG. 5, each of the fibers passes a rotatable roller or fixed roller or curved surface (not visible in FIG. 5, but located under the retention cap 190), then passes by the guide wall 114 before angling toward an anchor point comprising an alternative tensioning mechanism 138. In this embodiment, the tensioning mechanisms again comprise a pair of tension adjustment pins 192 mounted in pin blocks 194. In this embodiment, however, each pin block only has a single slot, whereas each pin block depicted in, for example, FIGS. 3 and 4, included a pair of slots. The pin blocks again comprise an integral part of, or are mounted on, a rotating lower actuator 122 (e.g., see the rotating lower actuator 122 of FIG. 8 in incorporated U.S. Patent Publication No. 2014/0336573). Preferably, each tuner pin 192 again includes a fiber hole to facilitate attaching the fiber to the tuner pin prior to "tuning" (i.e., tensioning) the pull wire.

Figure 6:
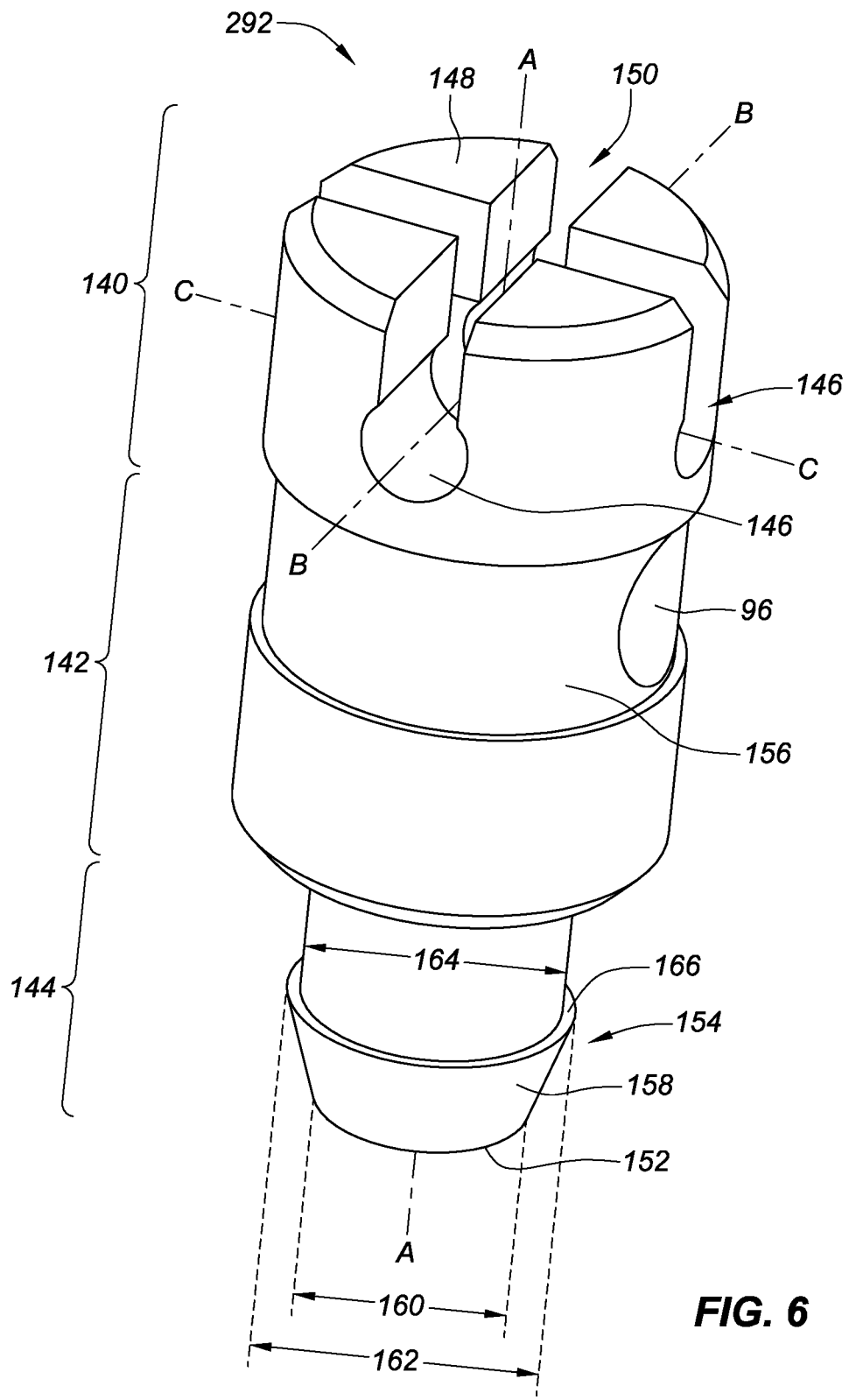
FIG. 6 is a schematic view of a tuning pin comprising one or more slots for a locking pin and a hold down element, consistent with embodiments of the present disclosure.

FIG. 6 is a schematic view of a tuning pin comprising one or more slots for a locking pin and a hold down element, consistent with embodiments of the present disclosure. Generally, 140, 340 can refer to a head portion of a tuning pin, 142, 342 can refer to a body portion of a tuning pin, and 144, 344 can refer to a tip portion of a tuning pin. As shown in FIG. 6, the tuning pin 292 can include a head portion 140, a body portion 142, and a tip portion 144. The head portion 140, the body portion 142, and the tip portion 144 can be integrated into a single element (e.g., machined from a unitary piece of material) or separate elements combined together (e.g., welded or otherwise secured together). The tuning pin 292 can also have a longitudinal axis defined by the line AA.

Figure 7A:
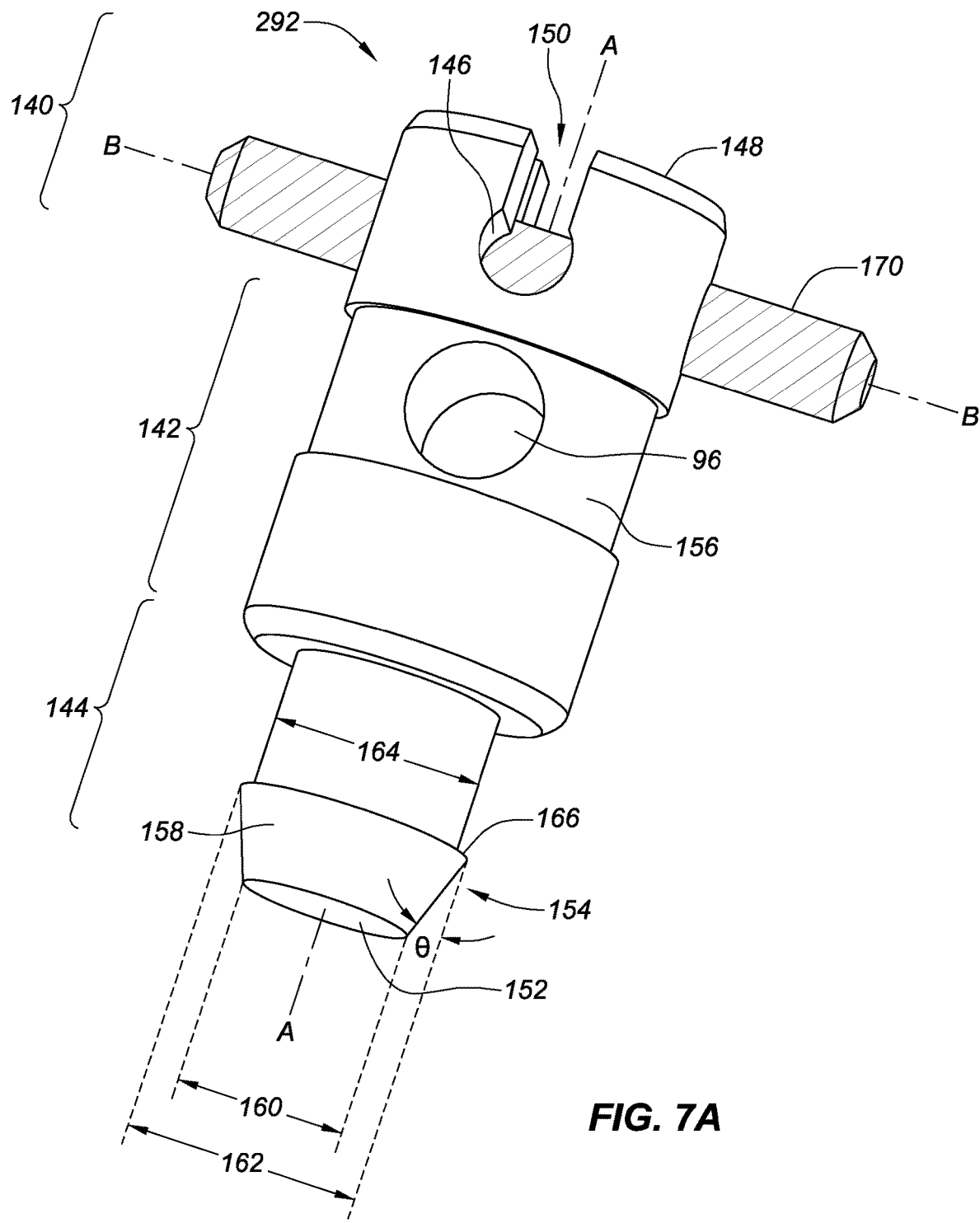
FIG. 7A is a schematic view of the tuning pin of FIG. 6 including a locking pin, consistent with embodiments of the present disclosure.
Figure 7B:
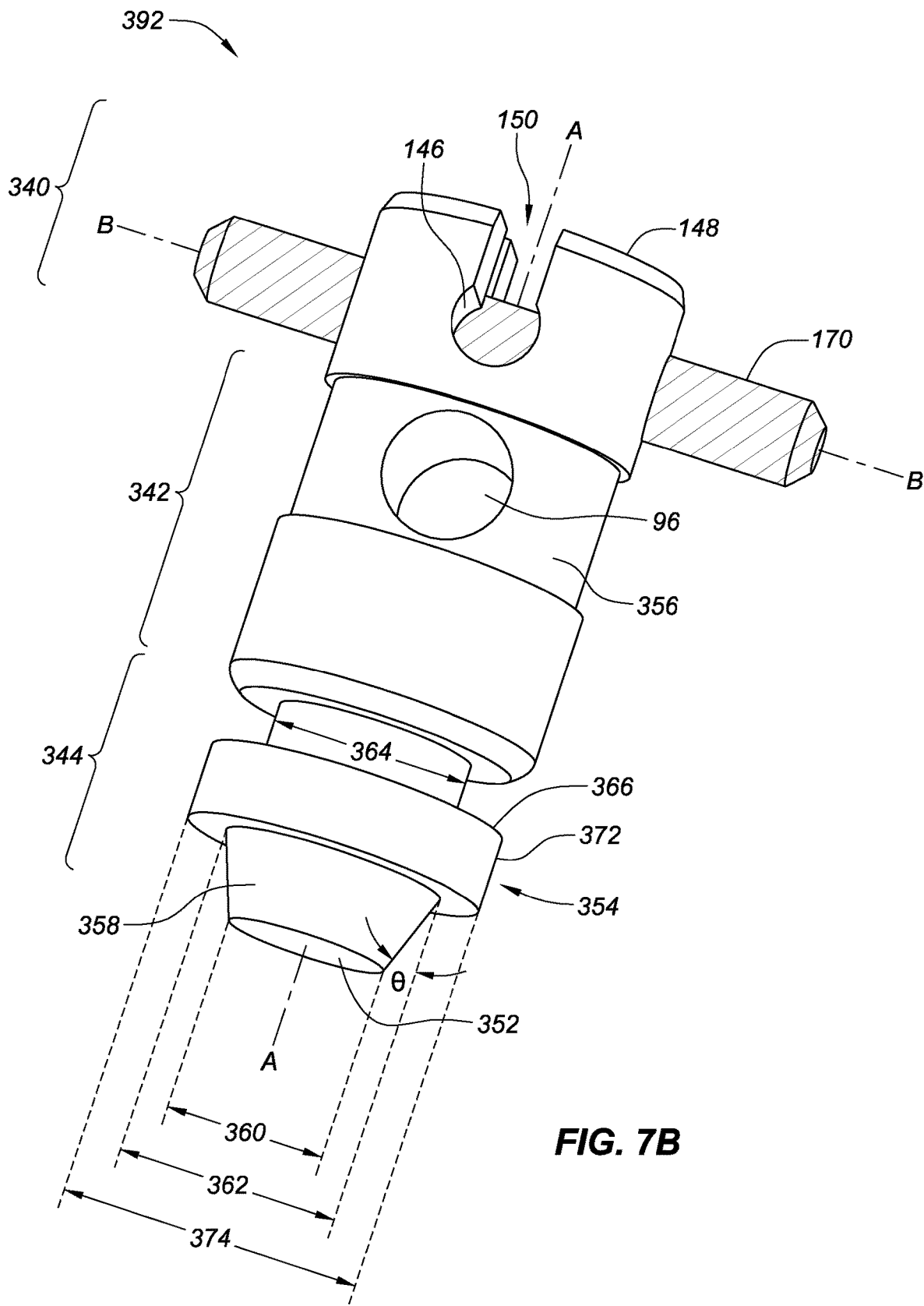
FIG. 7B is a schematic view of a tuning pin including a locking pin similar to FIGS. 6-7A with an exemplary hold down element, consistent with embodiments of the present disclosure.

The head portion 140 can include one or more openings 146 for a locking pin (shown in FIGS. 7A-B). In the embodiment shown in FIG. 6, the one or more openings 146 are tubular which can facilitate the coupling with a locking pin of similar shape (e.g., tubular). The one or more openings 146 can be, for example, a hole or a channel. The one or more openings 146 can be any suitable shape (longitudinal with a square, a trapezoidal, or a triangular cross-section). The one or more openings 146 can be, for example, perpendicular to the longitudinal axis defined by the line AA.

The head portion 140 of the tuning pin 292 can include a proximal end 148, where the head portion 140 can include one or more slots 150 and one or more openings 146. The body portion 142 can include a fiber channel or hole 96, and the tip portion 144 can have a distal end 152 and can include the hold down element 154.

Figure 8:
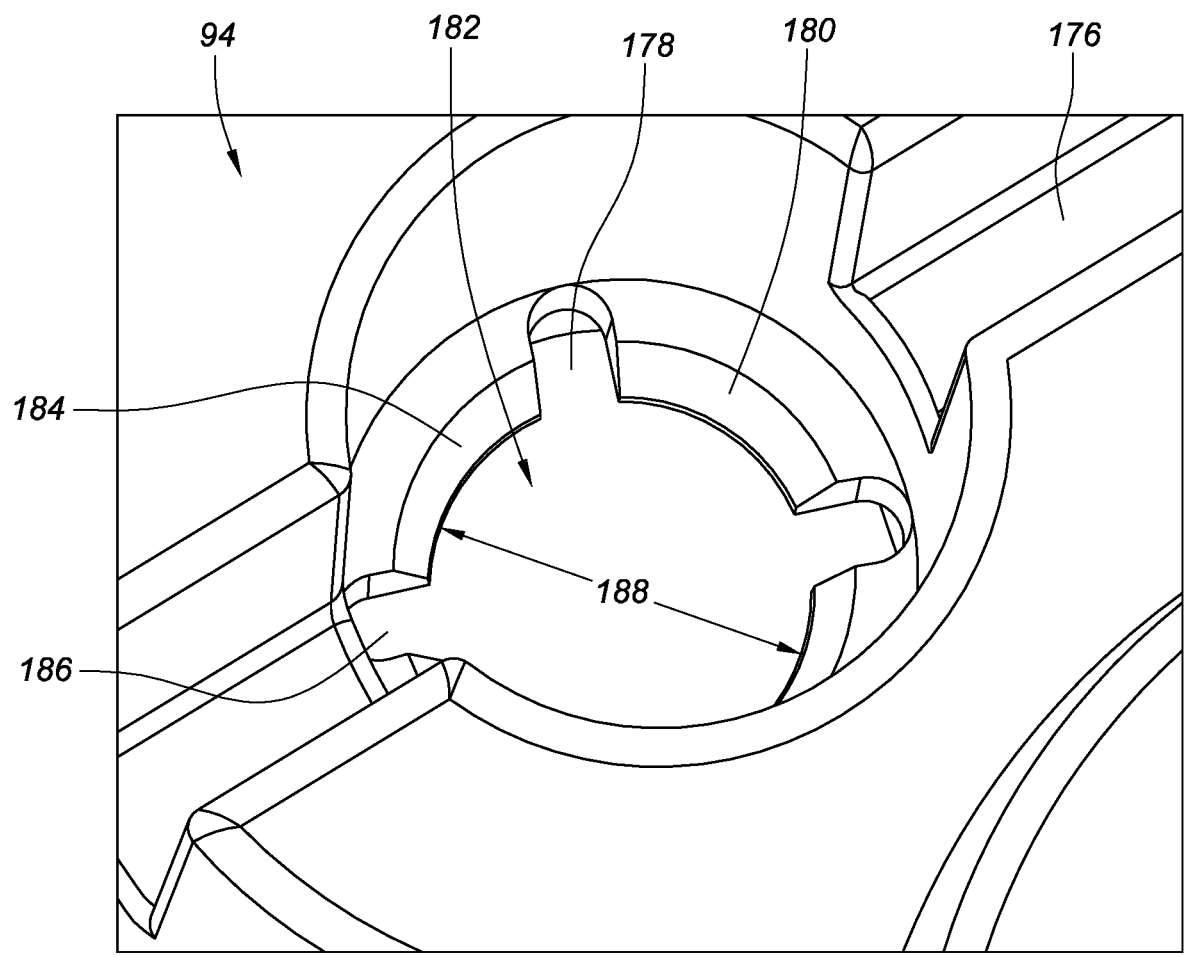
FIG. 8 is a schematic view of a portion of a pin block configured to couple with the tuning pin and the locking pin of FIGS. 6-7, consistent with embodiments of the present disclosure.
Figure 9:
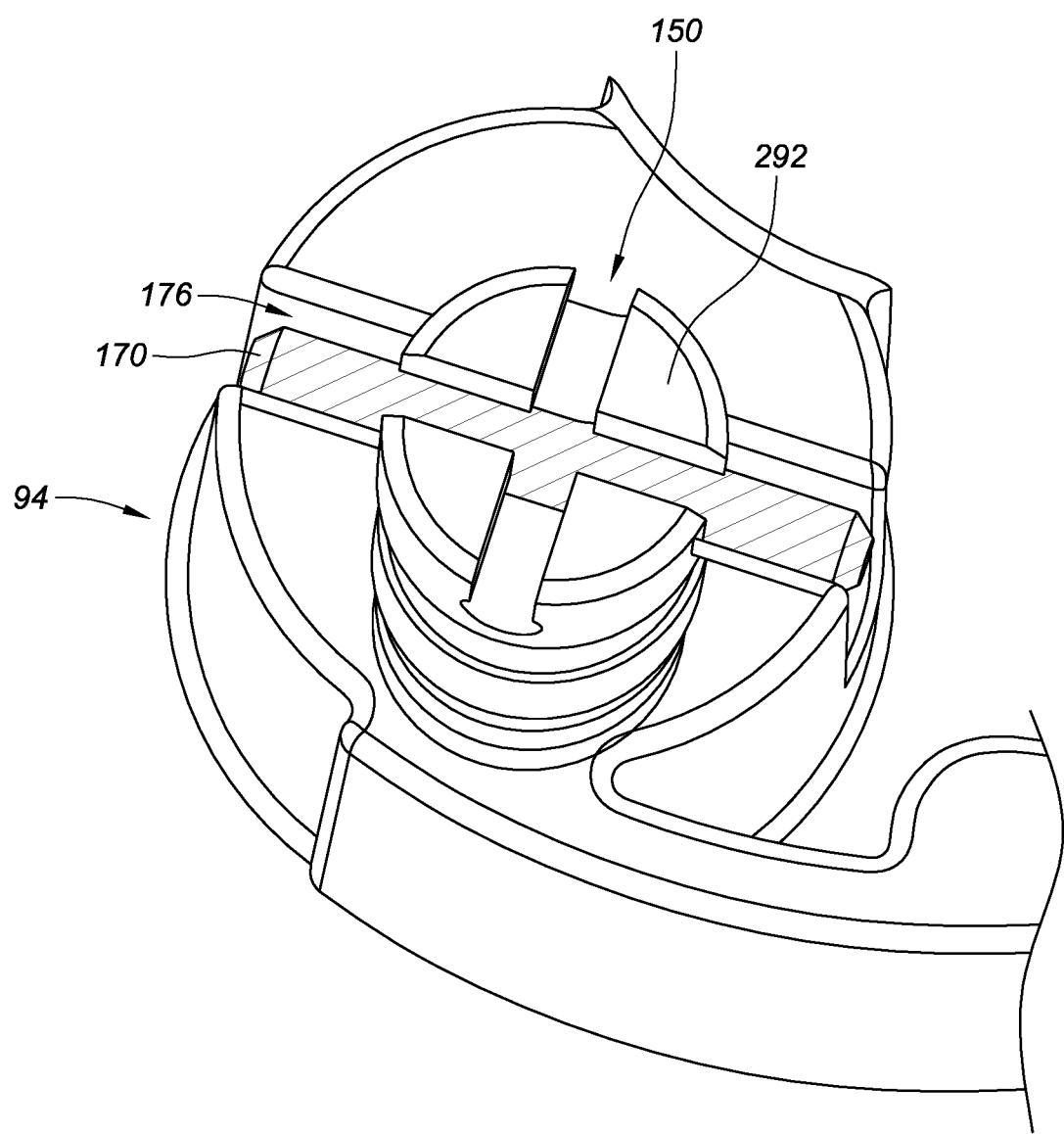
FIG. 9 is a schematic view of a partial cutaway portion of a pin block with the tuning pin and the locking pin of FIGS. 6-7, consistent with embodiments of the present disclosure.

The one or more slots 150 in the head portion 140, can be used to adjust the position or angle of the tuning pin 292 with respect to a pin block (e.g., pin block 194 shown in FIG. 5 and pin block 94 in FIGS. 8-9). For example, a tool (e.g., a screwdriver, not shown) can be coupled with the one or more slots 150 and rotate the tuning pin 292 about the longitudinal axis defined by the line AA. The one or more openings 146 can be configured to receive a locking pin (e.g., the locking pin 170 shown in FIGS. 7A-B and 9).

The head portion 140 can be configured to flex, bend, or otherwise accommodate the insertion of the locking pin (e.g., the locking pin 170 shown in FIGS. 7A-B and 9) into one of the one or more openings 146. The locking pin 170 can be inserted into the one or more openings in any suitable manner. For example, in one embodiment, the locking pin can be positioned by passing through one of the one or more slots 150 (e.g., as portions of the head portion bend/flex/move) until the locking pin 170 is coupled with one of the one or more openings 146. In another embodiment, the locking pin 170 can be inserted from one side of the head portion 140 into one of the one or more openings 146. For example, the locking pin 170 can be inserted into the head portion 140 along a line perpendicular to the longitudinal axis of the tuning pin 292 (e.g., the line BB or CC).

Continuing with FIG. 6, in addition to the fiber channel or hole 96, the body portion 142 can include a portion 156, proximate the hole 96, with a smaller diameter than the head portion 140. In some embodiments (not shown), the diameter of portion 156 can be equal to or smaller than the diameter 162 of the tip portion 144. The smaller diameter of the portion 156 can allow for windings of the fiber that is coupled with the tuning pin 292 (e.g., the fiber 36 in FIGS.

2-4 and 136 in FIG. 5) as the tuning pin 292 is adjusted when coupled with the pin block (see, e.g., pin block 94, 194 in FIGS. 3-5).

The tip portion 144 can include a hold down element 154 that includes an angled face 158 where a distal edge tip diameter 160 can be less than a proximal edge tip diameter 162 which creates the angled face 158 (e.g., chamfered). A diameter 164 of the tip portion 144 on the proximal side of the angled face 158 can be less than the proximal edge tip diameter 162. The difference between the diameter 164 and the proximal edge tip diameter 162 can create a surface 166. The surface 166, proximate the proximal edge tip diameter 162, can, for example, facilitate coupling with a portion of the pin block as described herein (see, e.g., FIGS. 11A-11C).

FIG. 7A is a schematic view of the tuning pin of FIG. 6 including a locking pin, consistent with embodiments of the present disclosure. As described above and shown in FIG. 6, the tuning pin 292 can include the one or more openings 146 for a locking pin 170 (shown in FIG. 7A) and the hold down element 154. In the embodiment shown in FIG. 7A, the one or more openings 146 are tubular which can facilitate the coupling with the locking pin 170 of similar shape (e.g., tubular). The one or more openings 146 can be, for example, a hole or a channel. The one or more openings 146 can be any suitable shape (longitudinal with a square, a trapezoidal, or a triangular cross-section).

The locking pin 170 can be placed into a corresponding opening of the one or more openings 146 by sliding the locking pin 170 in from the side or pressing the locking pin 170 down through one of the one or more slots 150 (e.g., the slots allow parts of the head portion 140 to bend, flex, and/or stretch to permit the locking pin 170 to couple with the corresponding one or more openings 146.

In the exemplary embodiment shown in FIGS. 6 and 7A, the locking pin 170 and the corresponding one or more openings 146 on the tuning pin 292 are shown as being cylindrical in shape. Any suitable shape can be used for the locking pin 170 and the corresponding one or more openings 146 including, for example, triangular, square, trapezoidal, oval, etc. (not shown). In another embodiment, the locking pin can be a fastener (e.g., a screw or a bolt) that couples with threads in the tuning pin 292, 392 and/or the pin block (e.g., pin block 94 in FIGS. 8 and 9).

FIG. 7A shows another view of the tip portion 144 of the tuning pin 292 in FIG. 6 including the angled face 158, the proximal edge tip diameter 162, and the distal edge tip diameter 160. An angle θ of the angled face 158 can vary. For example, a smaller difference between the proximal edge tip diameter 162 and the distal edge tip diameter 160 will generate a relatively small angle θ for the angled face 158 (e.g., a couple of degrees) making the angled face 158 nearly cylindrical. A larger difference between the proximal edge tip diameter 162 and the distal edge tip diameter 160 can result in a larger angle θ (e.g. 45°) for the angled face 158. Any angle that facilitates the insertion of the tuning pin 292 into the corresponding hold down element of the pin block is suitable.

FIG. 7B is a schematic view of another embodiment of a tuning pin, including a locking pin 170 with an exemplary hold down element 354, consistent with embodiments of the present disclosure. The tuning pin 392 can include a hold down element 354 with a different profile as compared to hold down element 154. A head portion 340 of the tuning pin 392 can include a proximal end 148, where the head portion 340 can include one or more slots 150 and one or more openings 146. The body portion 342 can include a fiber channel or hole 96, and the tip portion 344 can have a distal end 352 and can include the hold down element 354. Further, the body portion 342 can include a portion 356 proximate the hole 96 with a smaller diameter than the head portion 340 and/or the tip portion 344. The smaller diameter can allow for windings of the fiber that is coupled with the tuning pin 392 (e.g., the fiber 36 in FIGS. 2-4 and in FIG. 5) as the tuning pin 392 is adjusted when coupled with the pin block (see, e.g., pin block 94, 194 in FIGS. 3-5). The head portion 340, the body portion 342, and the tip portion 344 can be integrated into a single element (e.g., machined from a unitary piece of material) or separate elements combined together (e.g., welded or otherwise secured together).

In FIG. 7B a tip portion 344 can include (similar to the tuning pin 292 in FIG. 7A) an angled face 358, a distal edge tip diameter 360, and a proximal edge tip diameter 362 plus an additional element 372. An angle θ of the angled face 358 can vary. For example, a smaller difference between the proximal edge tip diameter 362 and the distal edge tip diameter 360 will generate a relatively small angle θ for the angled faced 358 (e.g., a couple of degrees) making the angled face 358 nearly cylindrical. A larger difference between the proximal edge tip diameter 362 and the distal edge tip diameter 360 can result in a larger angle θ (e.g. 45°) for the angled face 358. Any angle that facilitates the insertion of the tuning pin 392 into the corresponding feature (e.g. a recess, socket) of the pin block is suitable.

The hold down element 354 can include the element 372 with a different diameter (e.g., wider than the widest part of the angled face 358 of a tip portion 344). The different diameter 374 of the element 372 can facilitate coupling with a corresponding feature on the pin block (e.g., a socket or a recess) to prevent and/or limit movement of the tuning pin 392 in the longitudinal direction of the tuning pin 392 (e.g., along a longitudinal axis of the tuning pin represented by the line AA). A diameter 364 of the tip portion 344 on the proximal side of the hold down element 354 can be less than the diameter 374 of the element 372. The difference between the diameter 364 and the diameter 374 of the element 372 can create a surface 366 on the proximate side of element 372. The surface 366 can, for example, facilitate coupling with a portion of the pin block.

FIG. 8 is a schematic view of a portion of a pin block configured to couple with the tuning pin and the locking pin of FIGS. 6-7A/B, consistent with embodiments of the present disclosure. The tuning pin 92, 292, 392 can be coupled with the pin block 94 and the locking pin 170 can be coupled with the tuning pin 92, 292,392 and the pin block 94 that is part of an inner actuator (e.g., inner actuator 60 of FIG. 4). The locking pin 170 can prevent the tuning pin 92, 292, 392 from rotating from a set position (e.g., the combination of the locking pin 170, coupled with the tuning pin 92, 292, 392 and the pin block 94, together can be an anti-rotation element).

In the embodiment shown in FIG. 8, there is one channel 176 in the pin block 94 that can couple with the locking pin 170. In other embodiments, the pin block 94 can have more than one channel 176 to couple with the locking pin 170 which can allow for additional adjustment options of the tuning pin 92, 292,392. For example, the locking pin 170 can be coupled with the tuning pin 92, 292, 392 using any of the one or more openings one or more openings 146. In some embodiments, a locking pin that couples with more than one channel can be used (e.g., a locking pin shaped like an "X" or a "+" or other configuration, or two separate locking pins where the openings are arranged to allow the locking pins to pass each other (e.g., at different locations/levels in the head portion).

The view of the pin block 94 shown in FIG. 8 also includes a plurality of reliefs 178 between a plurality of flanges 180 in an opening 182 of the pin block 94. The plurality of reliefs 178 and the plurality of flanges 180 can facilitate the pin block 94 coupling with, for example, the hold down element 154 of the tuning pin 292 (see FIGS. 6-7A) or the hold down element 354 of the tuning pin 392 (see FIG. 7B). The plurality of reliefs 178 can facilitate insertion of the tip portion 144 or 344 of the tuning pin 292 or 392 into the opening 182 of the pin block 94 by allowing the plurality of flanges 180 to flex/bend/deflect as the tuning pin is inserted into the opening 182. Once the angled face 158 or 358 of the tip portion 144 or 344 of the tuning pin is inserted past the plurality of flanges 180, the tuning pin can be held in place in the pin block 94, with respect to the longitudinal axis, by the surface 166 (see FIGS. 6-7A) or the surface 366 (see FIG. 7B) of the tip portion 144 or 344 of the tuning pin 292 or 392, where the surface interacts with the plurality of flanges 180.

The plurality of flanges 180 can be configured to facilitate insertion of the tuning pin 292 or 392 into the pin block 94 and prevent removal of the tuning pin from the pin block. For example, the plurality of flanges 180 can have an flange edge face 184 angled as shown in the embodiment of FIG. 8. The plurality of flanges 180 can also have a bottom face 186. After the tuning pin 292 or 392 is inserted into the opening 182 of the pin block 94 as described above, the surface 166 or 366 of the tip portion 144 or 344 of the tuning pin 292 or 392 can couple with the bottom face 186 of the plurality of flanges 180 to prevent longitudinal movement of the tuning pin.

A diameter 188 can be slightly smaller than a diameter 164 or 364 of a tip portion 144 or 344 above a hold down element 154 or 354 of a tuning pin 292 or 392. This can facilitate coupling of the tuning pin with the pin block as described herein.

FIG. 9 is a schematic view of a partial cutaway portion of a pin block with the tuning pin and the locking pin of FIGS. 6-7, consistent with embodiments of the present disclosure. With the tuning pin 292 inserted into the opening (e.g., 182 in FIG. 8) of the pin block 94, the locking pin 170 can be coupled with the tuning pin 292, 392 which can be coupled with the pin block 94 as shown in FIG. 9.

FIG. 9 shows the tuning pin 292, 392 coupled with the pin block 94, where the locking pin 170 is in place in the one or more openings 146 of the tuning pin 292 or 392. As described herein, the tuning pin 292, 392 can be placed into the pin block 94 that is part of an inner actuator (e.g., inner actuator 60 of FIG. 4). For example, the tuning pin 292, 392 can be placed in the pin block 94 by inserting the tuning pin 292, 392 into the opening 182 of the pin block 94. After the tuning pin 292, 392 is inserted into the pin block 94, the tuning pin 292, 392 can be rotated to tighten a tension of a fiber (e.g., fiber 36 in FIGS. 4-5) that is coupled with the tuning pin 292, 392. The tuning pin 292, 392 can be rotated until one of the slots 150 lines up with the channel 176 in the pin block 94. Once aligned, the locking pin 170 can be coupled with the tuning pin 292, 392 and the pin block 94 (e.g., inserted into the one or more slots 150 and the channel 176 and/or slid, along the channel 176 of the pin block 94, into the one or more openings 146 of the tuning pin 292, 392 preventing rotational movement of the tuning pin 292, 392 with respect to the pin block 94.

Figure 10:
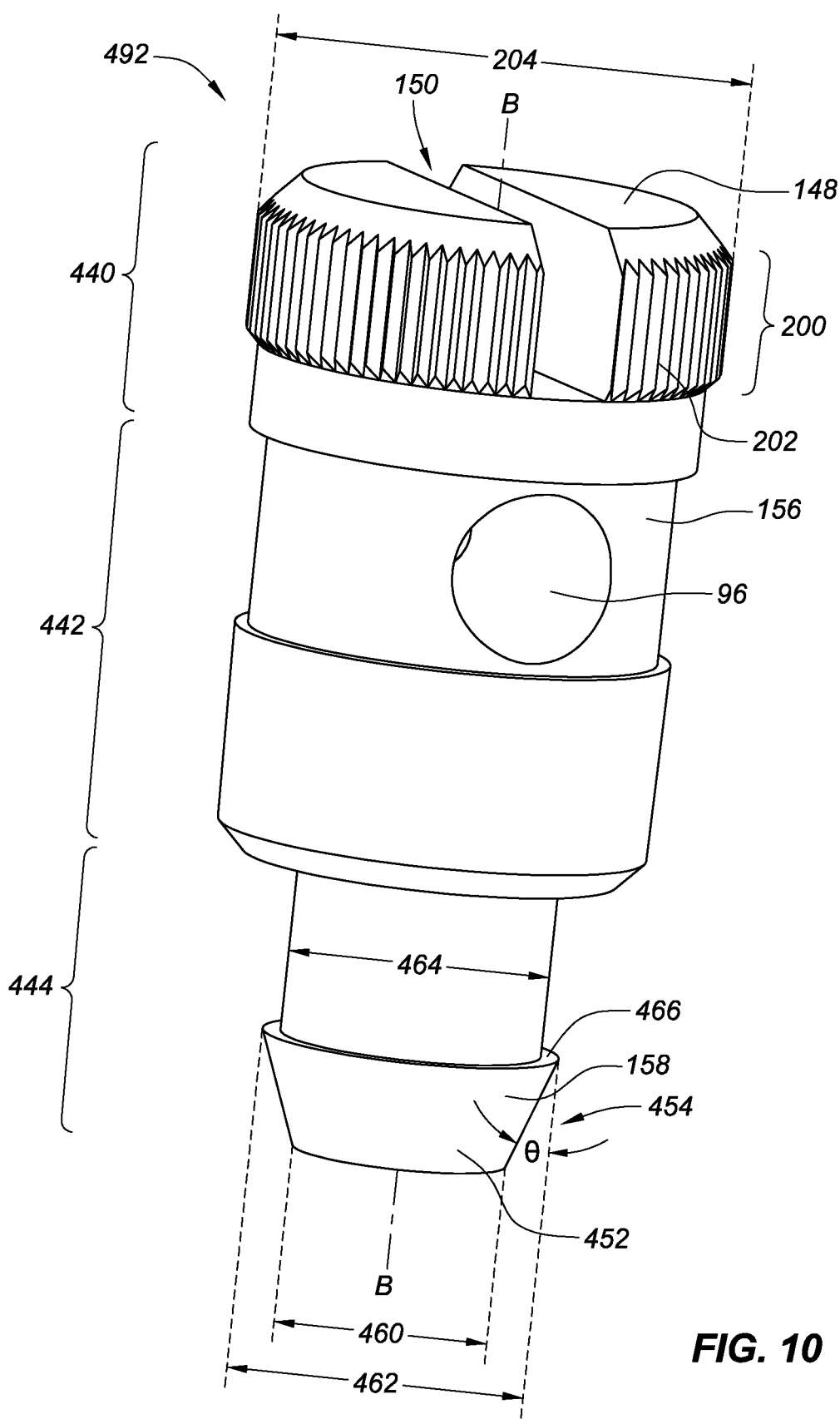
FIG. 10 is a tuning pin with an anti-rotation element and a hold down element, consistent with embodiments of the present disclosure.

FIG. 10 is a tuning pin with an anti-rotation element and a hold down element, consistent with embodiments of the present disclosure. The tuning pin 492 can include an anti-rotation element 200 where the anti-rotation element 200 can be an outwardly-facing surface that is a portion of the tuning pin 492. The outwardly-facing surface can be, for example, roughened or textured, coated, knurled, serrated, or undulating to increase friction between the outwardly-facing surface and a pin block (e.g., a pin block 294 in FIGS. 11A-C. The embodiment shown in FIG. 10 includes an outwardly-facing surface that is knurled (e.g., a knurled surface). The knurled surface can include a plurality of ridges (or teeth) 202. A portion of the plurality of ridges 202 can engage with a surface of the pin block.

In other embodiments, the surface of the pin block (e.g., pin block 294 in FIGS. 11A-C) that can correspond to the outwardly-facing surface of the tuning pin 492 can be roughened or textured, coated, knurled, serrated, or undulating to increase friction between the outwardly-facing surface of the tuning pin and the pin block.

The tuning pin 492 can include a head portion 440 and a proximal end 148, where the head portion 440 can include one or more slots 150 and an anti-rotation element 200, a body portion 442 where the body portion 442 can include a fiber channel or hole 96, and a tip portion 444 and a distal end 452, where the tip portion 444 can include the hold down element 454. The head portion 440, the body portion 442, and the tip portion 444 can be integrated into a single element (e.g., machined from a unitary piece of material) or separate elements combined together (e.g., welded or otherwise secured together).

In some embodiments the anti-rotation element 200 can be a knurled surface, where the knurled surface includes a plurality of ridges 202 on a circumferential surface of the head portion 440. The plurality of ridges 202 of the knurled surface can couple with the pin block (not shown in FIG. 10, but similar to the arrangement of the tuning pin 492 and the pin block 294 in FIGS. 11A-C). The combination of a diameter 204 of the head portion 440 and the knurled surface 200 can be sized to facilitate contact between the plurality of ridges 202 and the pin block 294. The contact between the plurality of ridges 202 and the pin block 294 can increase friction between the tuning pin 492 and the pin block 294 to prevent undesired rotational movement (e.g., about the longitudinal axis defined by the line AA) of the tuning pin 492. The friction force between the tuning pin 492 and the pin block 294 can still be overcome with a tool (e.g., a screwdriver) for adjustment of a fiber (e.g., fiber 36) coupled with the tuning pin 492.

Similar to the tuning pin 292 shown in FIGS. 6-7A, the tuning pin 492 can include a hold down element 454. The tuning pin 492 can include the tip portion 444 with an angled face 158, a proximal edge tip diameter 462, and a distal edge tip diameter 460. An angle θ of the angled face 158 can vary. For example, a smaller difference between the proximal edge tip diameter 462 and the distal edge tip diameter 460 will generate a relatively small angle for the angled faced 158 (e.g., a couple of degrees) making the angled face 158 nearly cylindrical. A larger difference between the proximal edge tip diameter 462 and the distal edge tip diameter 460 can result in a larger angle (e.g. 45°) for the angled face 158. Any angle that facilitates the insertion of the tuning pin 492 into the opening of the pin block (e.g., pin block 294 in FIGS. 11A-C) is acceptable. Further, a diameter 464 of the tip portion 444 on the proximal side of the angled face 158 can be less than the proximal edge tip diameter 462. The difference between the diameter 464 and the proximal edge tip diameter 462 can create a surface 466. The surface 466, proximate the proximal edge tip diameter 462, can, for example, facilitate coupling with a portion of the pin block (see, e.g., FIGS. 11A-11C).

Figure 11A:
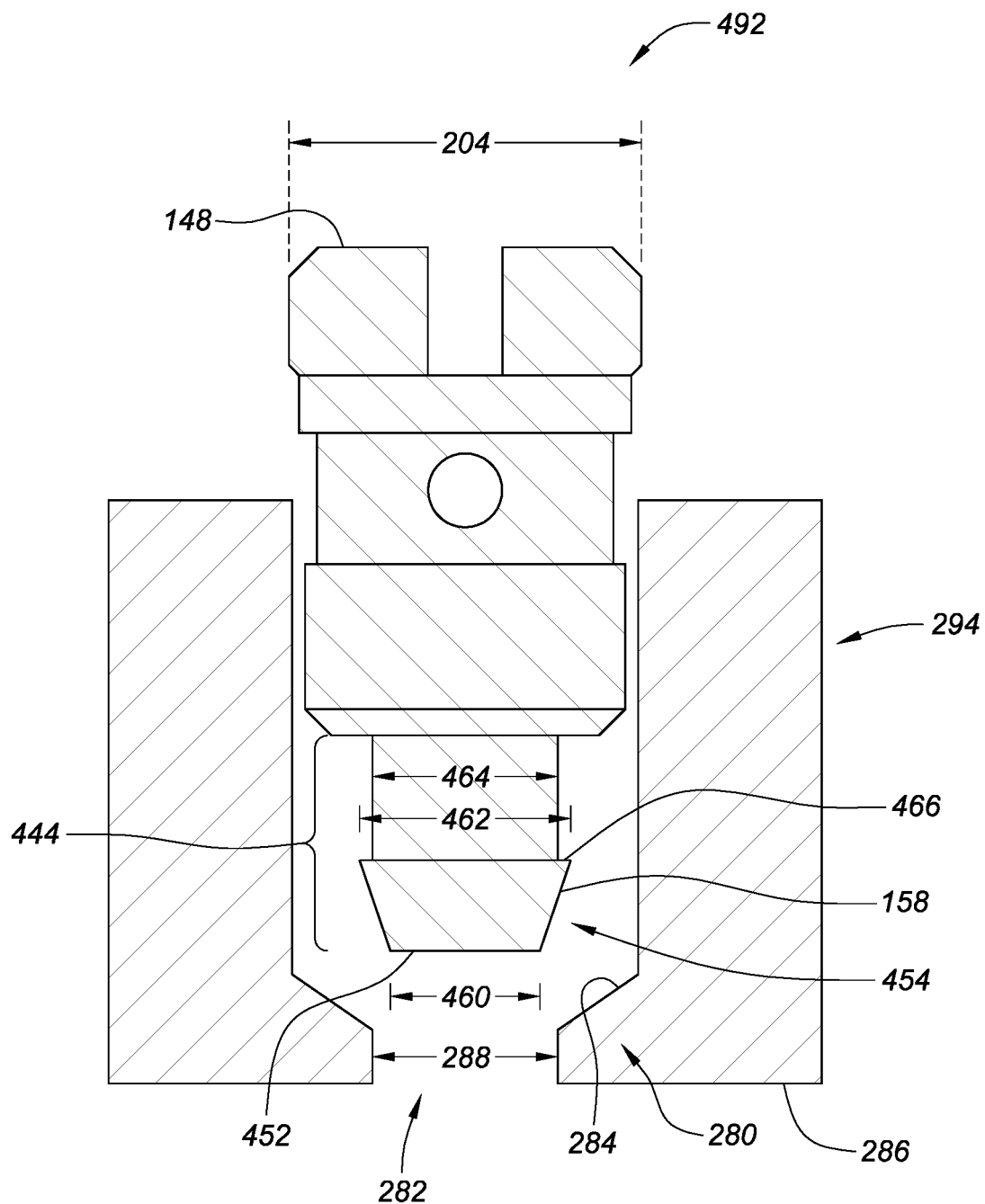
FIG. 11A is cross-sectional view of a tuning pin with a hold down element for limiting longitudinal movement of the tuning pin in relation to a pin block, consistent with embodiments of the present disclosure.

FIG. 11A is a cross-sectional view of a tuning pin with a hold down element for limiting longitudinal movement of the tuning pin in relation to a pin block, consistent with embodiments of the present disclosure. The tuning pin 492 can include a proximal end 148 and a distal end 452. In some embodiments, a hold down element 454 for limiting longitudinal movement of the tuning pin in relation to the pin block can be located proximate the distal end 452 of the tuning pin 492. In other embodiments the hold down element 454 can be located proximate the proximal end 148 or between the proximal end 148 and the distal end 452 (e.g., in the middle of the tuning pin 492).

The hold down element 454 can be, for example, one or more elements that limit the longitudinal movement of the tuning pin 492 by preventing the tuning pin 492 from longitudinally sliding more than a distance in relation to the pin block 294. The distance can be an amount due to variations in fit within a tolerance for the tuning pin 492 and the pin block 294 specifications.

In the exemplary embodiment shown in FIG. 11A, the hold down element 454 can couple with a portion of the pin block 294 (see FIG. 8 and related discussion) where a proximal edge tip diameter 462 on the tip portion 444 of the tuning pin 492 is larger than a diameter 288 of the opening 282 in the pin block 294 (see FIG. 8 and related discussion).

The tuning pin 492 can also include a feature that facilitates coupling the tuning pin 492 with the pin block 294. For example, the tuning pin 492 can include the tip portion 444 proximate the distal end 452 where the tip portion 444 includes a distal edge tip diameter 460 and a proximal edge tip diameter 462. The distal edge tip diameter 460 and the proximal edge tip diameter 462 can be different diameters. As shown in the exemplary embodiment of FIG. 11A, a distal edge tip diameter 460 is less than a proximal edge tip diameter 462 which creates an angled face 158 (e.g., chamfered). The angled face 158 of the tip portion 444 can facilitate the tuning pin 492 coupling with a portion of the pin block 294 to engage the hold down element (e.g., the angled face 158 assists with the insertion of the tip portion 444 of the tuning pin 492 into the opening 282 of the pin block 294).

Figure 11B:
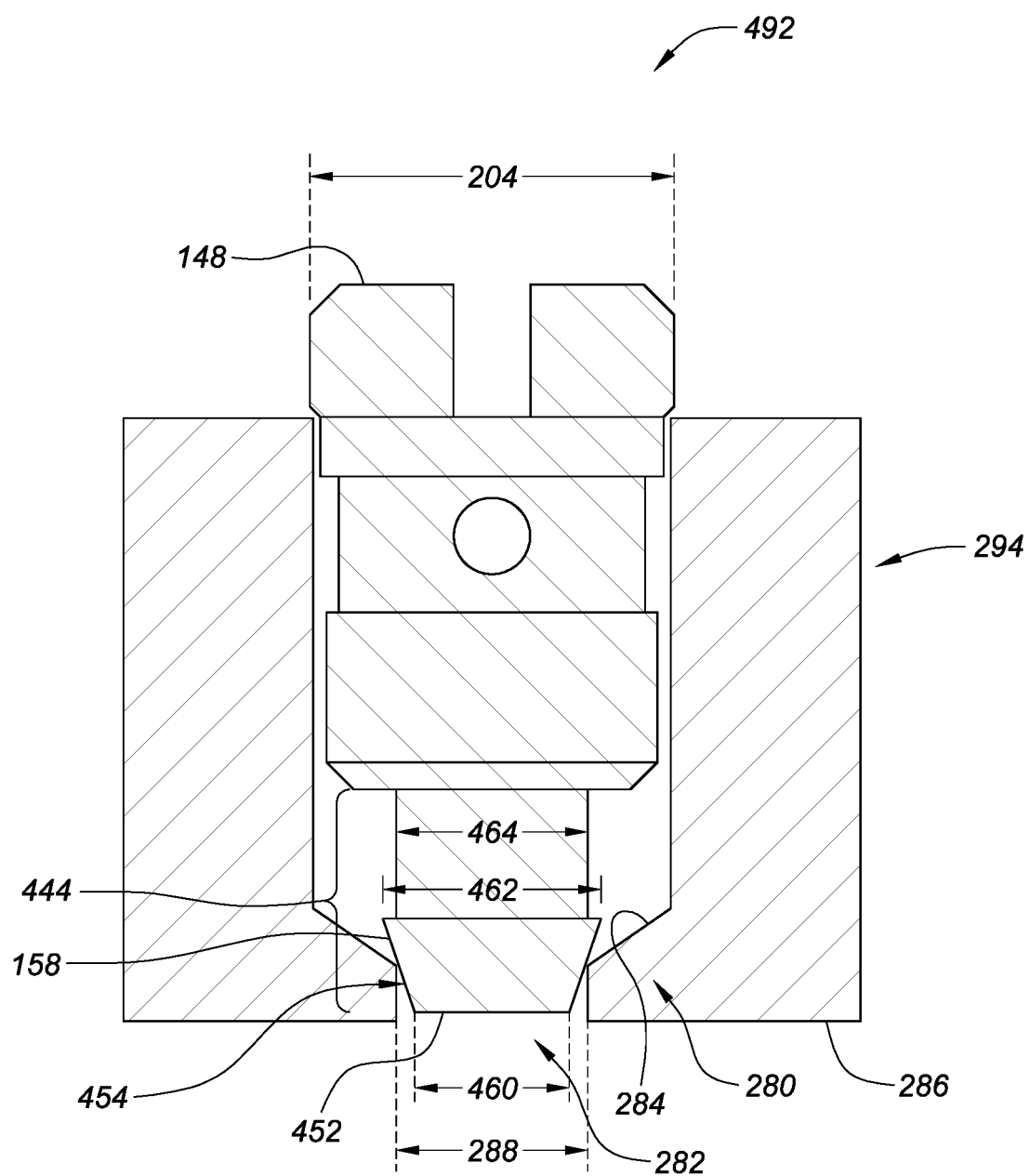
FIG. 11B is a cross-sectional view of the tuning pin with the hold down element for limiting longitudinal movement of FIG. 11A as the hold down element is moved into place with the pin block of FIG. 11B, consistent with embodiments of the present disclosure.

FIG. 11B is a cross-sectional view of the tuning pin with the hold down element for limiting longitudinal movement of FIG. 11A as the hold down element is moved into place with the pin block of FIG. 11B, consistent with embodiments of the present disclosure. As seen in FIG. 11B, the angled face 158 is starting to contact the plurality of flanges 280 on the pin block 294 (see FIG. 8 and related discussion). As described herein, the angled face 158 can facilitate the insertion of the tip portion 444 of the tuning pin 492 through the opening 282 of the pin block 294.

Figure 11C:
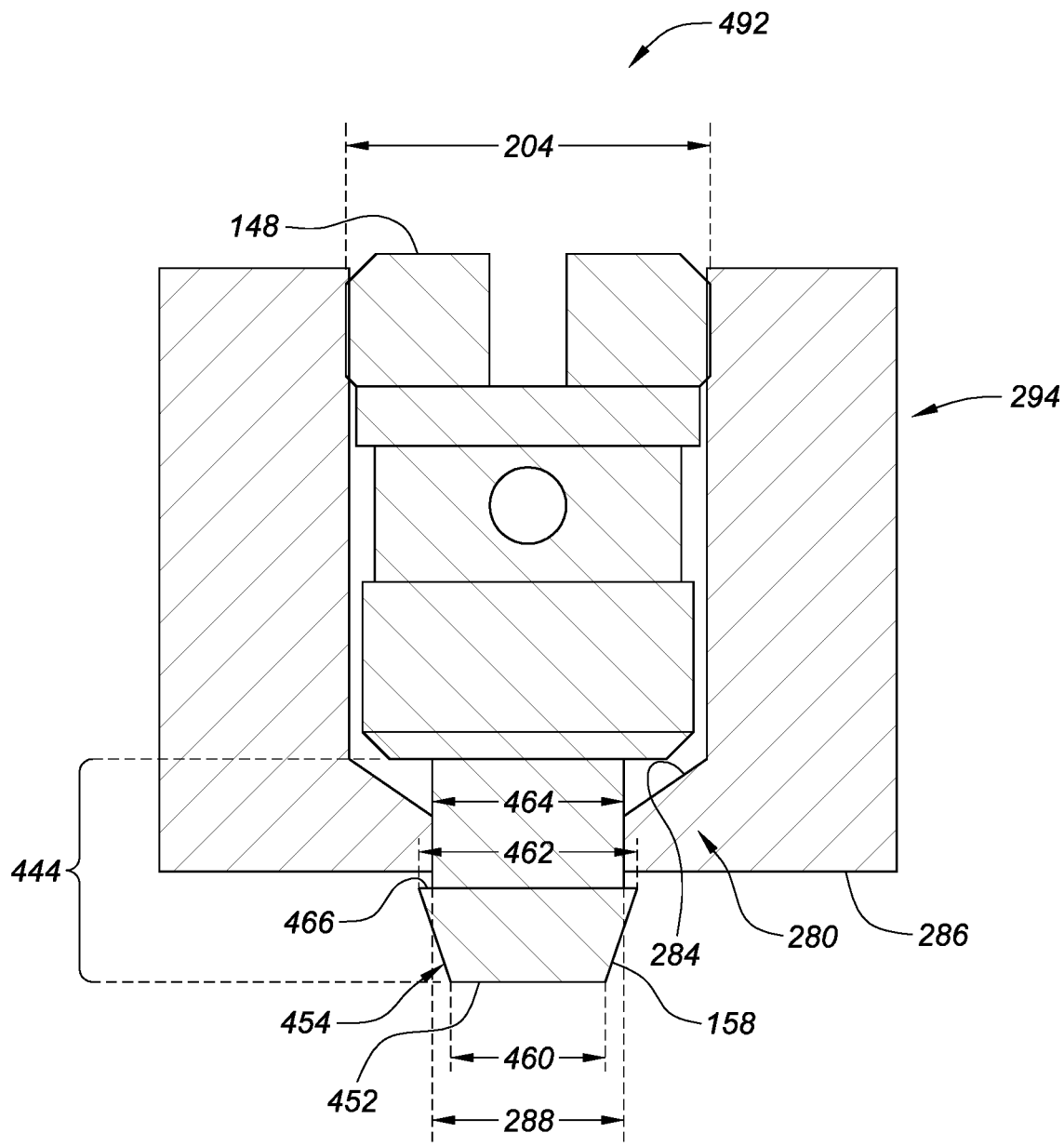
FIG. 11C is a cross-sectional view of the tuning pin with the hold down element for limiting longitudinal movement of FIGS. 11A-B with the hold down element is coupled with the pin block of FIGS. 11A-B, consistent with embodiments of the present disclosure.

FIG. 11C is a cross-sectional view of the tuning pin with the hold down element for limiting longitudinal movement as shown in FIGS. 11A-B where the hold down element is coupled with the pin block of FIGS. 11A-B, consistent with embodiments of the present disclosure. FIG. 11C shows the hold down element 454 coupled with the pin block 294, where the surface 466 of the angled face 158 has been inserted past the plurality of flanges 280 on the pin block 294.

Figure 12A:
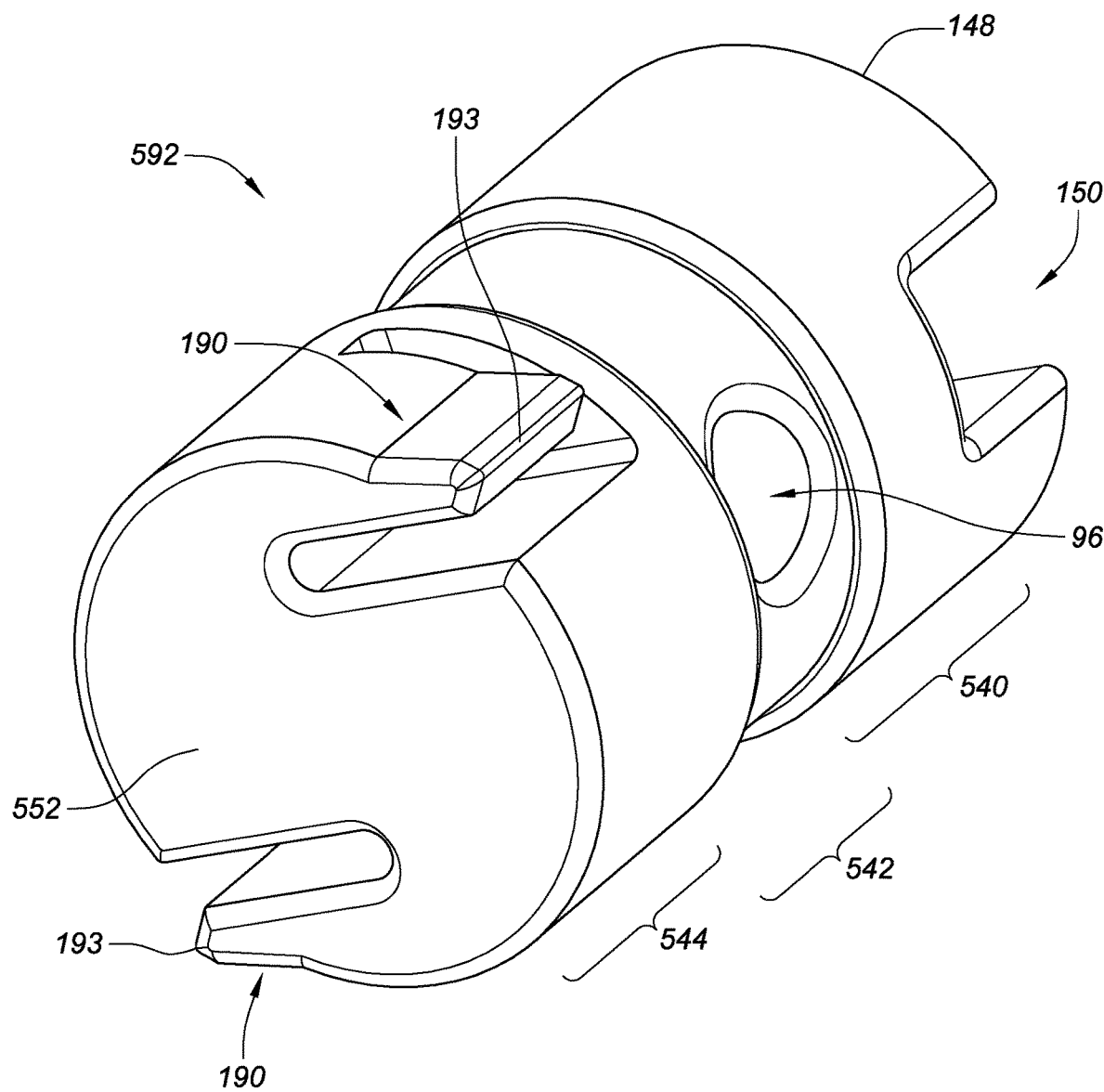
FIG. 12A is a schematic bottom and side view of a tuning pin with an anti-rotation element including two teeth, consistent with embodiments of the present disclosure.

FIG. 12A is a schematic bottom and side view of a tuning pin with an anti-rotation element including two teeth, consistent with embodiments of the present disclosure. The tuning pin 592 can include a head portion 540 and a proximal end 148, where the head portion 540 can include a slot 150, a body portion 542 that can include a fiber channel or hole 96, and a tip portion 544 and a distal end 552, where the tip portion 544 can include one or more flexible members 190 that can each include a tooth 193. The head portion 540, the body portion 542, and the tip portion 544 can be integrated into a single element (e.g., machined from a unitary piece of material) or separate elements combined together (e.g., welded or otherwise secured together).

The tip portion 544 can include one or more flexible members 190 and each of the flexible members 190 can include a tooth 193 (e.g., two flexible members, so two teeth as shown in the embodiment depicted in FIG. 12A) where the teeth 193 are configured to engage a portion of a pin block (described in greater detail below). The one or more teeth 193 can be coupled with or be integral with a corresponding flexible member 190. The flexible member 190 can be coupled with or be integral with the tip portion 544 of the tuning pin 592 and the flexible member 190 can be configured to deflect/flex/bend to facilitate coupling of the one or more teeth 193 with the pin block (see FIG. 14 and related discussion). The flexible member 190 can be coupled to the tip portion 544 or it can be integral with the tip portion 544. While the embodiment of FIG. 12A includes two teeth 193, any suitable number of teeth can be included on the tip portion 544. In other embodiments, the teeth can be located on another portion (e.g., the head portion 540) of the tuning pin 592.

An interaction of the pin block and the flexible member 190/the teeth 193 can function like a ratchet mechanism. For example, the ratchet mechanism can be similar to that of a cable tie (e.g., zip tie, hose tie) that permits a one-way movement and prevents movement in the opposite direction (e.g., the flexible section of the cable tie with teeth/notches can slide through a head with a pawl where the pawl engages the teeth/notches preventing the flexible section from sliding in the other direction). The tuning pin 592 can be rotated in one direction (e.g., counter-clockwise) to tighten a fiber (e.g. fiber 36 in FIG. 4) and the ratchet mechanism can prevent the tuning pin 592 from loosening (e.g., rotating clockwise) the fiber (e.g., fiber 36 in FIG. 4).

Similar to the description of the tuning pin of FIG. 6, the head portion 540 can include a slot 150. The slot 150 can be used to engage a tool (e.g., a screwdriver) to turn the tuning pin 592. In some embodiments, more than one slot 150 can be included in the head portion 540 and/or the head portion can be configured to accept another type of tool (e.g., a Phillips screwdriver).

Figure 12B:
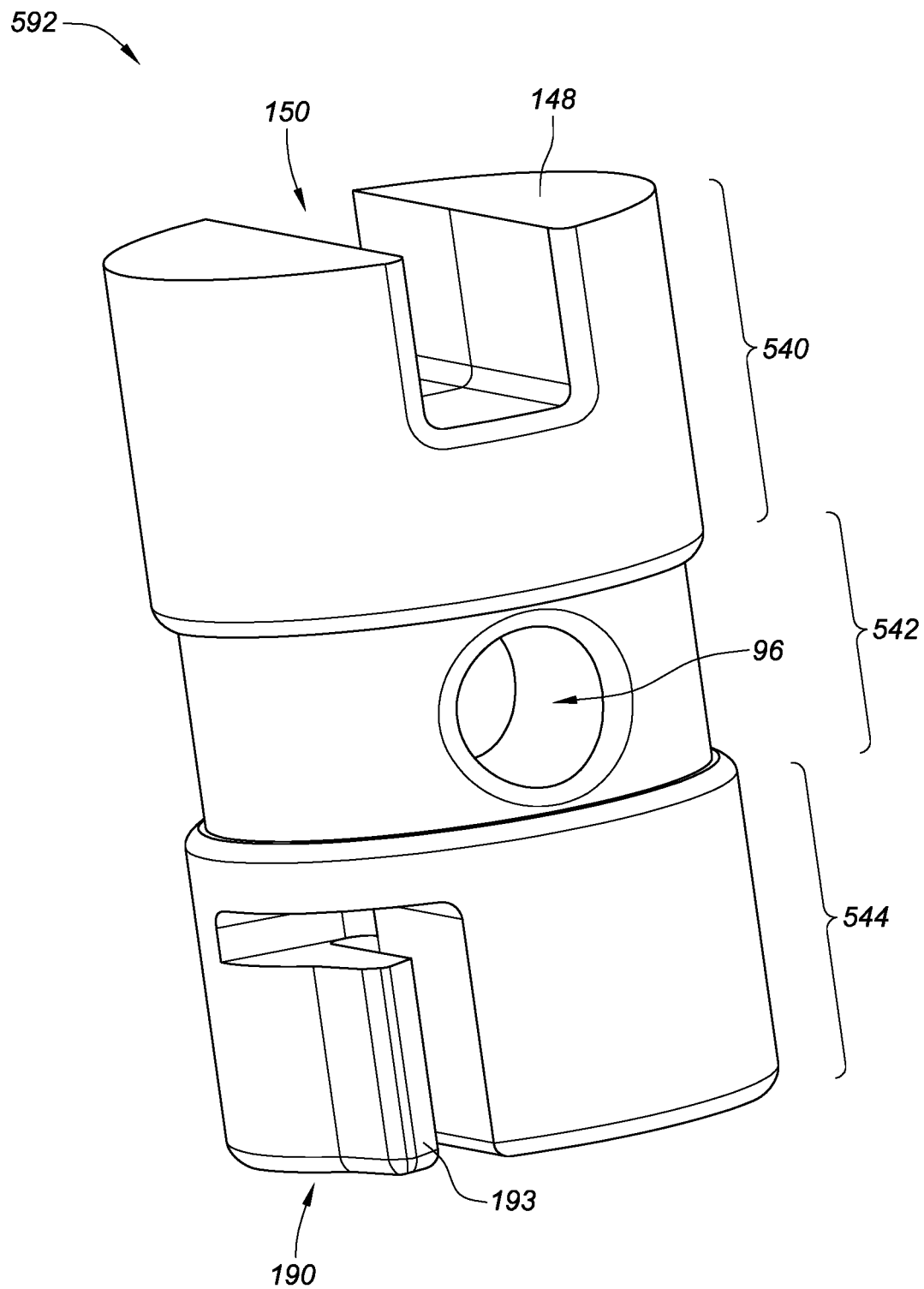
FIG. 12B is a schematic side and top view of the tuning pin of FIG. 12A, consistent with embodiments of the present disclosure.

FIG. 12B is a schematic side and top view of the tuning pin of FIG. 12A, consistent with embodiments of the present disclosure. As discussed above with reference to FIG. 12A, the flexible member 190 can be coupled with the tip portion 544 of the tuning pin 592 (only one of the two flexible members 190 is visible in FIG. 12B). The flexible member 190 can include a tooth 193 (one tooth 193 is hidden from view in FIG. 12B) that can couple with the pin block (not shown in FIG. 12B, see, e.g., pin block 394 in FIG. 14). The flexible member 190 can be configured to allow flexing/bending/deflecting with respect to the tip portion 544 to facilitate adjustment of the tuning pin 592 as the tuning pin 592 is rotated in the pin block (e.g., the one or more teeth 193 move as the each flexible members 190 flexes/bends/deflects as directed by the configuration of the pin block).

Figure 13A:
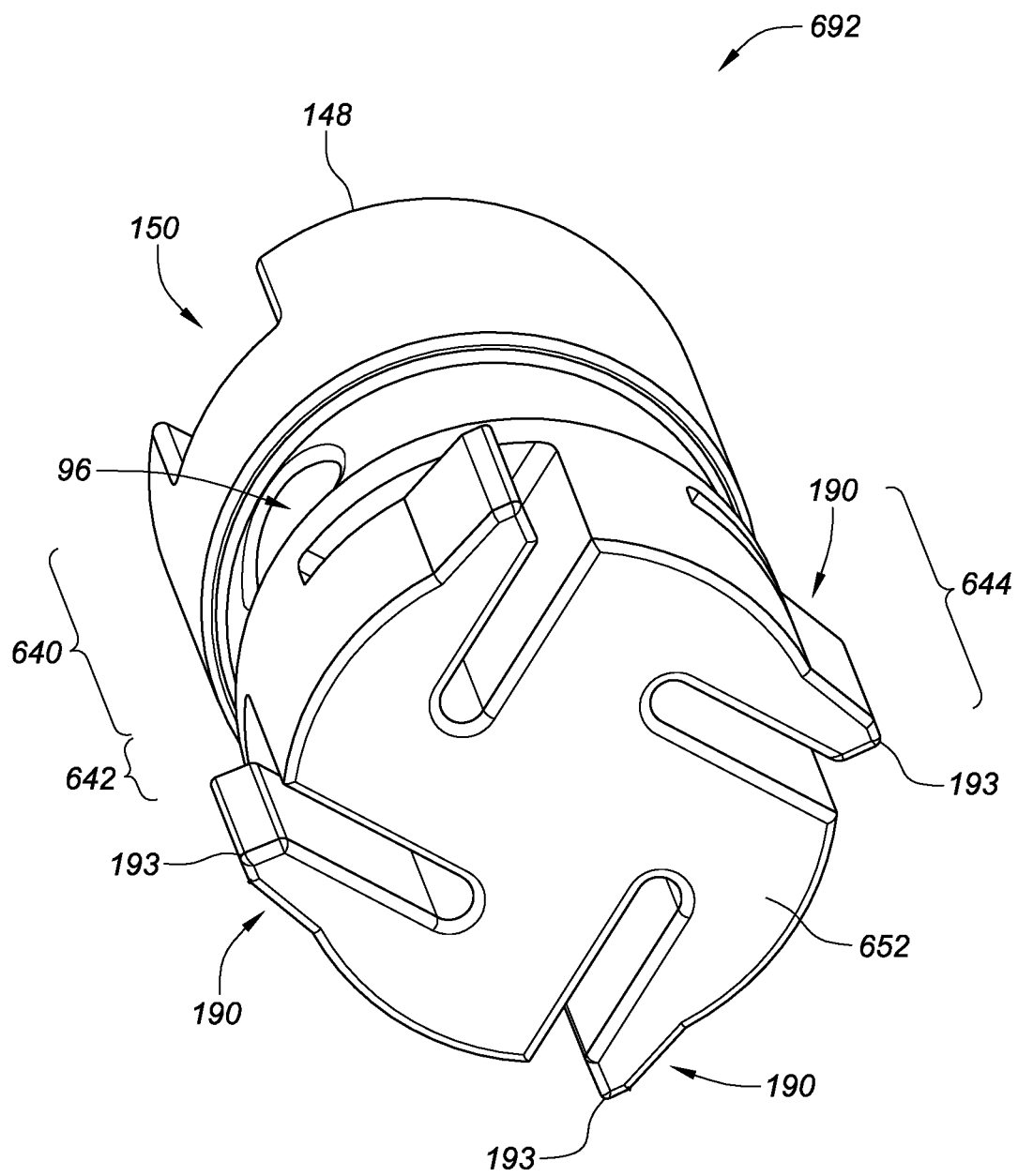
FIG. 13A is a schematic bottom and side view of a tuning pin with an anti-rotation element including four teeth, consistent with embodiments of the present disclosure.

FIG. 13A is a schematic bottom and side view of a tuning pin with an anti-rotation element including four teeth, consistent with embodiments of the present disclosure. The tuning pin 692 can include a head portion 640 and a proximal end 148, where the head portion 640 can include a slot 150, a body portion 642 that can include a fiber channel or hole 96, and a tip portion 644 and a distal end 652, where the tip portion 644 can include the four teeth 193. The head portion 640, the body portion 642, and the tip portion 644 can be integrated into a single element (e.g., machined from a unitary piece of material) or separate elements combined together (e.g., welded or otherwise secured together).

Figure 14:
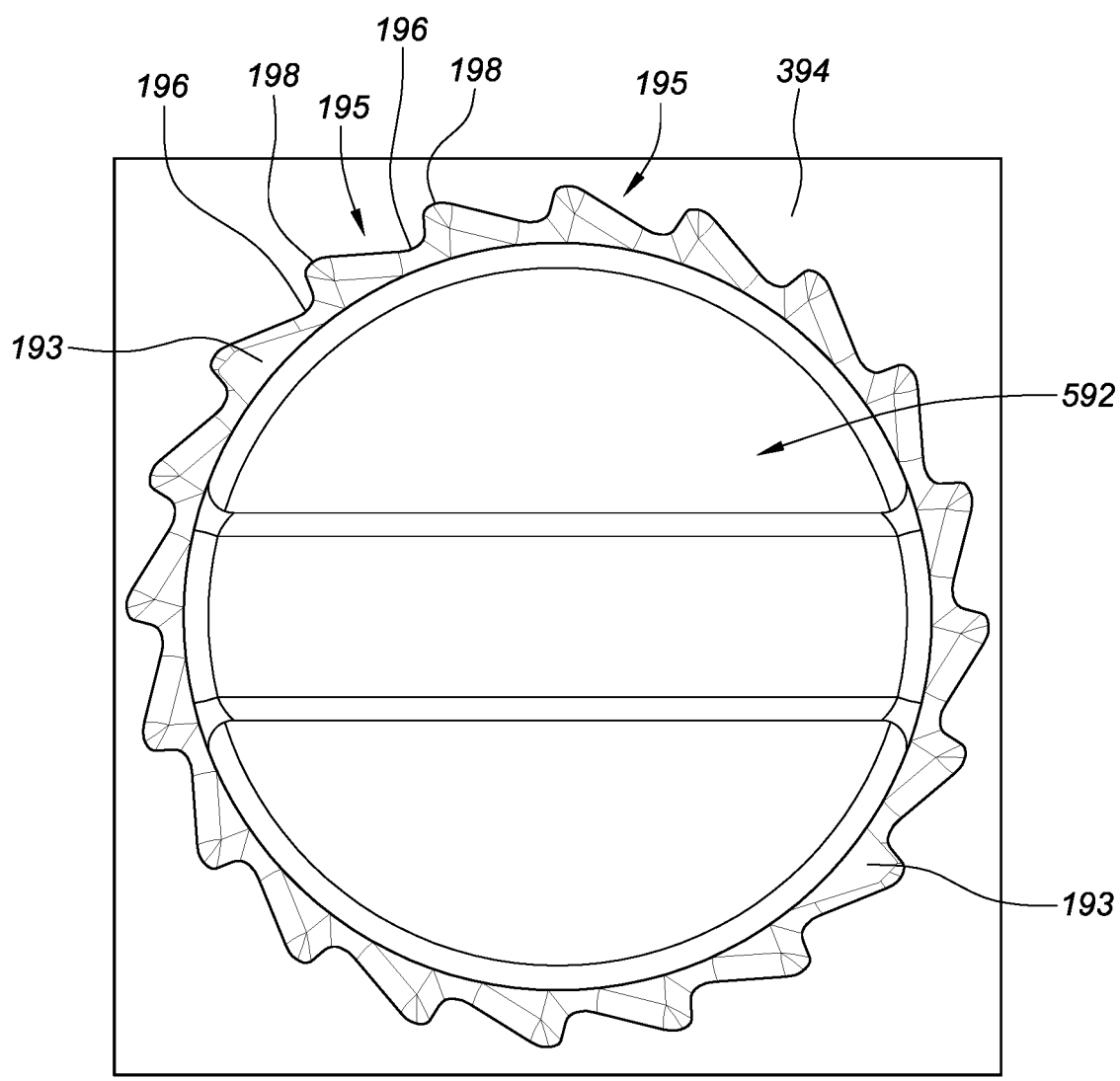
FIG. 14 is a schematic bottom view of the tuning pin of FIGS. 12A-B with a portion of a pin block including a plurality of notches, consistent with embodiments of the present disclosure.
Figure 15:
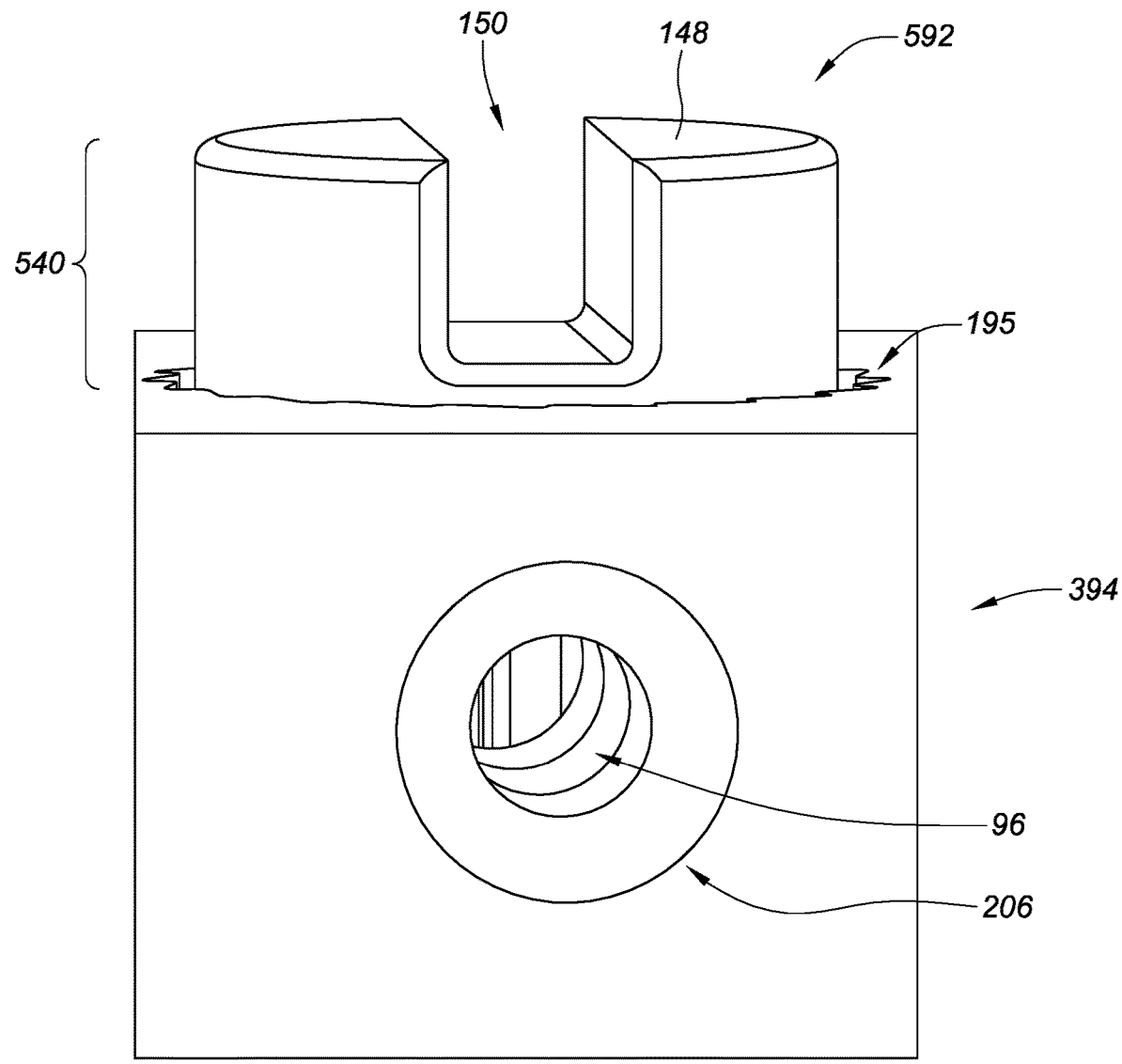
FIG. 15 is a schematic top and side view of the tuning pin of FIGS. 12A-B coupled with the pin block portion of FIG. 14, consistent with embodiments of the present disclosure.

Similar to the embodiment shown in FIG. 12A, the embodiment shown in FIG. 13A the tip portion 644 can include the four teeth 193 where each of the teeth 193 are configured to engage a portion of a pin block (e.g., pin block 394 in FIGS. 14-15, described in greater detail herein). Each of the teeth 193 can be mounted on or be integral with a corresponding flexible member 190. The flexible member 190 can be coupled with or integral with the tip portion 644 of the tuning pin 692 and can be configured to deflect/flex/bend to facilitate coupling of the one or more teeth 193 with the pin block. While the embodiment of FIG. 13A includes four teeth 193, any suitable number of teeth can be included on the tip portion 644. In other embodiments, the teeth can be located on another portion (e.g., the head portion 640) of the tuning pin 692.

Similar to the tuning pin 592 of FIGS. 12A-B, the interaction of the pin block and the flexible member 190/the teeth 193 of the tuning pin 692 can function like a ratchet mechanism. For example, the ratchet mechanism of the head portion 640 can be similar to that of a cable tie (e.g., zip tie, hose tie) that permits a one-way movement and prevents movement in the opposite direction (e.g., the flexible section of the cable tie with teeth/notches can slide through a head with a pawl where the pawl engages the teeth/notches preventing the flexible section from sliding in the other direction). The tuning pin 692 can be rotated in one direction (e.g., counter-clockwise) to tighten a fiber (e.g. fiber 36 in FIG. 4) coupled with the tuning pin 692 and the ratchet mechanism can prevent the tuning pin 692 from loosening (e.g., rotating clockwise) the fiber.

Similar to the description of the tuning pins 292 and 592 of FIGS. 6 and 12A, the head portion 640 can include a slot 150. The slot 150 can be used to engage a tool (e.g., a screwdriver) to turn the tuning pin 692. In some embodiments, more than one slot 150 can be included in the head portion 640 and/or the head portion can be configured to accept another type of tool (e.g., a Phillips screwdriver).

Figure 13B:
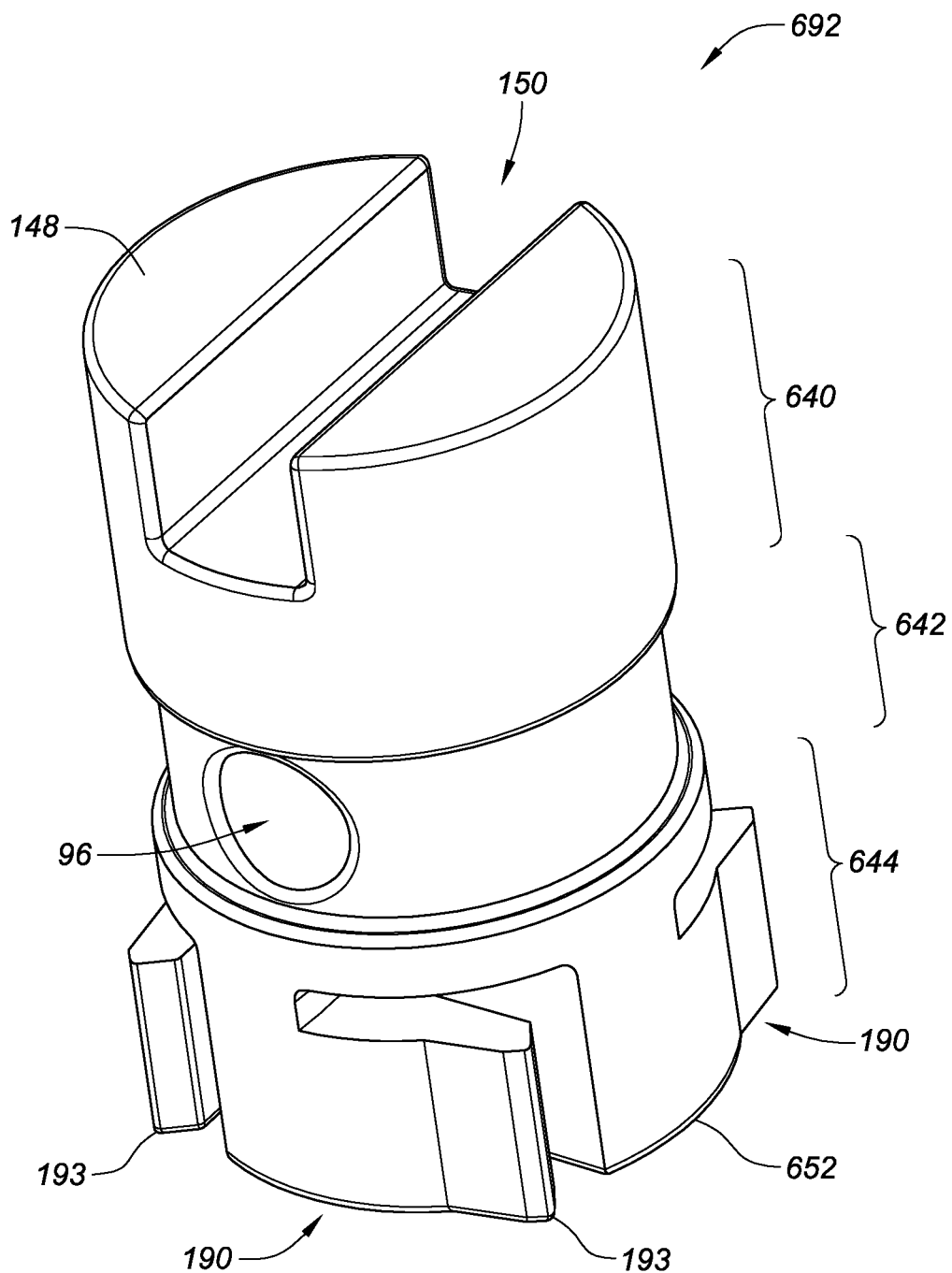
FIG. 13B is a schematic side and bottom view of the tuning pin of FIG. 13A, consistent with embodiments of the present disclosure.

FIG. 13B is a schematic side and bottom view of the tuning pin of FIG. 13A, consistent with embodiments of the present disclosure. As discussed above with reference to FIG. 13A, each of the flexible members 190 can be coupled with or integral with the tip portion 644 of the tuning pin 692. Each of the flexible members 190 can include one or more teeth 193 (one tooth is hidden from view in FIG. 13B) that can engage the pin block (not shown in FIG. 13B, see pin block 394 in FIGS. 14-15). Each of the flexible members 190 are configured to allow flexing/bending/deflecting with respect to the tip portion 644 to facilitate adjustment of the tuning pin 692 as the tuning pin 692 is rotated in the pin block (e.g., the one or more teeth 193 move as each flexible member 190 flexes/bends/deflects as directed by the configuration of the pin block).

FIG. 14 is a schematic bottom view of the tuning pin of FIGS. 12A-B with a portion of a pin block including a plurality of notches, consistent with embodiments of the present disclosure. The pin block 394 can include the plurality of notches 195 (not visible in FIG. 14, see FIG. 12A). The plurality of notches 195 can be configured to couple with the flexible member 190 and/or the teeth 193 on the tuning pin 592. The notches 195 can be shaped to facilitate rotation of the tuning pin 592 in one direction (e.g., clockwise or counter-clockwise) but not both directions when coupled with the pin block 394. In some embodiments, tuning pins with a different number of teeth (e.g., tuning pin 692 shown in FIG. 13A) can be used with the pin block 394.

As the tuning pin 592 is rotated in a permitted direction (e.g., the direction that is facilitated by the shape of the flexible members 190/the teeth 193 and the notches 195, such as counter-clockwise) the flexible members 190 can bend/flex/move to permit the teeth 193 of the flexible members 190 to clear a peak 196 of the notch 195 until the teeth 193 of the flexible member 190 rotates to a valley 198 of the next notch 195. For example, the gear notch and gear member arrangement can be similar to that found on a cable tie. The can allow the tuning pin 592 can be rotated in one direction (e.g., counter-clockwise) to tighten a fiber (e.g. fiber 36 in FIG. 4) coupled with the tuning pin and the ratchet mechanism can prevent the tuning pin 592 from loosening (e.g., rotating clockwise) the fiber.

FIG. 15 is a schematic top and side view of the tuning pin of FIGS. 12A-B coupled with the pin block portion of FIG. 14, consistent with embodiments of the present disclosure. A side and top view of the embodiment of FIG. 14 shows the tuning pin 592 coupled with the pin block 394. The head portion 540 can protrude above the pin block 394. As described above, the pin block 394 includes the notches 195 that can interact with the teeth (not visible in FIG. 15; see the teeth 193 in FIG. 14) of the tuning pin 592. The tuning pin 592 can include a slot 150 that can be used to adjust the rotational position of the tuning pin 592. The pin block 394 can include a hole 206 for a fiber (e.g., fiber 36 in FIG. 4) to pass through to couple with the tuning pin 592 through the hole 96.

With respect to any of the embodiments described in FIGS. 12A-15, other embodiments can include the ratcheting mechanism (e.g., the teeth) at the head portion of the tuning pin and a slot (or other configuration) can be incorporated between the flexible members so the tuning pin can be rotated. This arrangement can be similar to the embodiments described in FIGS. 6-10 with the locking pin and the surfaces that can be treated (e.g., textured, coated, knurled, serrated, or undulating) to limit the rotation of the tuning pin.

Although at least one embodiment of a tuning pin for a steering actuator has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system comprising:
   a catheter; and
   a steering actuator comprising a tuning pin, where the tuning pin comprises a head portion proximate a proximal end of the tuning pin, where the head portion comprises an anti-rotation element,
   a body portion distal the head portion, where the body portion comprises a through hole, and
   a tip portion distal the body portion and proximate a distal end of the tuning pin, wherein the tuning pin is configured to couple with a pin block in the steering actuator; and
   wherein the tip portion comprises a hold down element to limit longitudinal movement of the tuning pin in the pin block.

2. The system of claim 1, wherein the anti-rotation element comprises a channel and a locking pin, where the locking pin is configured to couple with the channel and a portion of the pin block.

3. The system of claim 1, wherein the anti-rotation element comprises a treatment of an outwardly-facing surface of the head portion where the treatment increases friction between the outwardly-facing surface and the pin block.

4. The system of claim 3, wherein the treatment is selected from the group consisting of the outwardly-facing surfacing being roughened, textured, knurled, coated, serrated, and undulating.

5. The system of claim 1, wherein the anti-rotation element comprises a ratchet mechanism, where the ratchet mechanism comprises one or more teeth on the head portion of the tuning pin and a plurality of notches on the pin block, where the plurality of notches are configured to couple with the teeth to limit the rotation of the tuning pin to a single direction.

6. The system of claim 1, wherein the anti-rotation element comprises a plurality of teeth on the pin block and the pin block comprises a pawl, where one or more of the teeth engage the pawl to limit the rotation of the tuning pin to a single direction.

7. The system of claim 1, wherein the pin block comprises a plurality of reliefs to facilitate insertion of the tuning pin into the pin block.

8. The system of claim 7, wherein the pin block comprises a plurality of flanges to facilitate insertion of the tuning pin into the pin block.

9. The system of claim 1, wherein the tuning pin comprises an angled face of the tip portion, where the tip portion includes a first diameter at a distal edge and a second diameter at a proximal edge and the second diameter is larger than the first diameter, and the body portion proximate the proximal edge is a third diameter less than the second diameter.

10. The system of claim 9, wherein the hold down element comprises interaction between the plurality of flanges and a surface proximate the proximal edge tip of the tuning pin.

* * * * *